US012350090B2

(12) United States Patent
Tu et al.

(10) Patent No.: US 12,350,090 B2
(45) Date of Patent: Jul. 8, 2025

(54) METHODS AND SYSTEMS FOR CONTROLLING MEDICAL DEVICES

(71) Applicant: SHANGHAI UNITED IMAGING HEALTHCARE CO., LTD., Shanghai (CN)

(72) Inventors: Jiali Tu, Shanghai (CN); Yecheng Han, Shanghai (CN); Linrong Zou, Shanghai (CN); Yifeng Zhou, Shanghai (CN); Xingyue Yi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 247 days.

(21) Appl. No.: 18/163,923

(22) Filed: Feb. 3, 2023

(65) Prior Publication Data

US 2023/0172577 A1    Jun. 8, 2023

Related U.S. Application Data

(63) Continuation of application No. PCT/CN2021/110409, filed on Aug. 3, 2021.

(30) Foreign Application Priority Data

Aug. 3, 2020  (CN) .......................... 202010767758.3
Oct. 18, 2020 (CN) .......................... 202011114024.1
Oct. 18, 2020 (CN) .......................... 202011114737.8

(51) Int. Cl.
*A61B 6/00*    (2024.01)
*A61B 6/08*    (2006.01)
(Continued)

(52) U.S. Cl.
CPC ................ *A61B 6/547* (2013.01); *A61B 6/08* (2013.01); *A61B 6/4435* (2013.01);
(Continued)

(58) Field of Classification Search
CPC ......... A61B 6/547; A61B 6/08; A61B 6/4435; A61B 6/4494; A61B 6/466; A61B 6/545;
(Continued)

(56) References Cited

U.S. PATENT DOCUMENTS

2008/0310583 A1    12/2008   Truyen et al.
2011/0249791 A1*   10/2011   Wang ..................... A61B 6/547
                                                      378/62

(Continued)

FOREIGN PATENT DOCUMENTS

CN        102551743 A      7/2012
CN        103040480 A      4/2013
(Continued)

OTHER PUBLICATIONS

Sheng, Bin et al., Virtual Reality Theoretical Foundation and Application Development Practice, Shanghai Jiao Tong University Press, 2019, 7 pages.
(Continued)

*Primary Examiner* — Edwin C Gunberg
*Assistant Examiner* — Richard O Toohey
(74) *Attorney, Agent, or Firm* — METIS IP LLC

(57) ABSTRACT

The present disclosure provides a method and system for controlling a medical device. The method for controlling the medical device may include: obtaining information related to the medical device and/or information related to a target object; controlling the medical device based on the information related to the medical device and/or the information related to the target object.

20 Claims, 15 Drawing Sheets

(51) Int. Cl.
  *A61B 6/46* (2024.01)
  *A61B 6/58* (2024.01)
  *G06T 13/20* (2011.01)
  *G06T 17/00* (2006.01)
  *G06V 10/25* (2022.01)

(52) U.S. Cl.
  CPC ............ *A61B 6/4494* (2013.01); *A61B 6/466* (2013.01); *A61B 6/545* (2013.01); *A61B 6/587* (2013.01); *G06T 13/20* (2013.01); *G06T 17/00* (2013.01); *G06V 10/25* (2022.01); *G06T 2210/41* (2013.01); *G06V 2201/034* (2022.01)

(58) Field of Classification Search
  CPC ......... A61B 6/587; A61B 6/54; A61B 6/4452; A61B 6/542; A61B 5/0033; A61B 5/7285; G06T 13/20; G06T 17/00; G06T 2210/41; G06V 10/25; G06V 2201/034
  See application file for complete search history.

(56) References Cited

U.S. PATENT DOCUMENTS

| | | |
|---|---|---|
| 2014/0348296 A1 | 11/2014 | Goossen et al. |
| 2017/0347979 A1 | 12/2017 | Fehre et al. |
| 2018/0247714 A1 | 8/2018 | Lee |
| 2020/0163550 A1 | 5/2020 | Igarashi et al. |
| 2022/0296200 A1 | 9/2022 | Wang et al. |

FOREIGN PATENT DOCUMENTS

| | | | |
|---|---|---|---|
| CN | 103908270 A | 7/2014 | |
| CN | 104799873 A | 7/2015 | |
| CN | 107644686 A | 1/2018 | |
| CN | 108766589 A | 11/2018 | |
| CN | 109276289 A | 1/2019 | |
| CN | 109549656 A | 4/2019 | |
| CN | 109692015 A | 4/2019 | |
| CN | 110742631 A | 2/2020 | |
| CN | 110811623 A | 2/2020 | |
| CN | 111275825 A | 6/2020 | |
| CN | 111772655 A | 10/2020 | |
| CN | 112071405 A | 12/2020 | |
| CN | 112274166 A | 1/2021 | |
| EP | 3662834 A1 * | 6/2020 | ............ G06V 20/64 |
| WO | 2010026791 A1 | 3/2010 | |
| WO | 2020115307 A1 | 6/2020 | |

OTHER PUBLICATIONS

The Extended European Search Report in European Application No. 21852413.0 mailed on Sep. 19, 2023, 9 pages.
International Search Report in PCT/CN2021/110409 mailed on Nov. 1, 2021, 7 pages.
Written Opinion in PCT/CN2021/110409 mailed on Nov. 1, 2021, 8 pages.
Ding, Guofu et al., Remote Operation Theory and Simulation of Material Handling Machinery Based on Virtual Reality, Southwestjiaotong University Press, 2007, 8 pages.
First Office Action in Chinese Application No. 202011114737.8 mailed on Dec. 29, 2023, 19 pages.

* cited by examiner

500

Obtaining identification information of at least one target ionization chamber selected from the one or more ionization chambers — 510

Adjusting the projection data based on the identification information, such that a first feature value of image data corresponding to a detection regions of the at least one target ionization chamber in the projection data is different from a second feature value of image data corresponding to detection regions of other ionization chambers, wherein the first feature value and the second feature value correspond to a same image feature — 520

Obtaining Module 610

Detection Region Determination Module 620

Projection Data Determination Module 630

Control Module 640

Candidate Ionization Chamber Determination Module 650

Target Ionization Chamber Determination Module 660

```
┌─────────────────────────────────────┐
│ Obtaining a virtual model of a medical │ ─── 710
│         treatment device             │
└─────────────────────────────────────┘
                  │
                  ▼
┌─────────────────────────────────────┐
│     Obtaining current movement       │ ─── 720
│ information of one of a first component │
│  of the medical treatment device and a │
│  second component of the virtual model │
└─────────────────────────────────────┘
                  │
                  ▼
┌─────────────────────────────────────┐
│  Controlling the other one of the first │
│   component of the medical treatment  │
│   device and the second component of  │
│   the virtual model to perform a same │ ─── 730
│    movement as the one of the first   │
│   component of the medical treatment  │
│   device and the second component of  │
│    the virtual model that obtains a   │
│          movement instruction         │
└─────────────────────────────────────┘
```

910 — Obtaining a model of an X-ray camera gantry based on a solid structure of the X-ray camera gantry, and simulating a corresponding model movement trajectory by using a model of the X-ray camera gantry based on a movement trajectory of the solid structure of the X-ray camera gantry

920 — Obtaining a movement instruction of a solid structure of a current X-ray camera gantry, the movement instruction including a target position that a component of the current X-ray camera frame needs to move to and related movement time information

930 — Causing the solid structure of the X-ray camera frame to reach the target position based on the movement instruction, and simulating, by the model of the X-ray camera frame, a movement trajectory of the model based on the movement instruction and the movement time information synchronously

940 — Displaying a simulation of the movement trajectory of the model on a display device

FIG. 9

METHODS AND SYSTEMS FOR CONTROLLING MEDICAL DEVICES

CROSS-REFERENCE TO RELATED APPLICATIONS

This application is a continuation of International Application No. PCT/CN/2021/110409, filed on Aug. 3, 2021, which claims priority of Chinese Patent Application No. 202010767758.3, filed on Aug. 3, 2020, Chinese Patent Application No. 202011114737.8, filed on Oct. 18, 2020, and Chinese Patent Application No. 202011114024.1, filed on Oct. 18, 2020, the contents of each of which are hereby incorporated by reference.

TECHNICAL FILED

The present disclosure generally relates to the field of a medical device, and in particular, to methods and systems for controlling a medical device.

BACKGROUND

With the development of science and technology level, the human need for medical treatment is increasing. The medical device may be an automated device for performing a medical treatment or a research task. The medical device may include a diagnostic device (e.g., an X-ray diagnostic device, a ultrasonic diagnostic device, a functional examination device, an endoscopic examination device, a nuclear medicine device, an experimental diagnostic device, and a pathological diagnostic equipment, etc.) for diagnosing a physiological state of a target object (e.g., a patient), a treatment device (e.g., a surgical bed, a contact therapy machine, a superficial therapy machine, a depth therapy machine, a semiconductor cold knife, a gas cold knife, a solid cold knife, a cardiac defibrillation pacing equipment, an artificial respirator, a ultrasonic nebulizer, etc.) for treating the target object (e.g., the patient), and an auxiliary device (e.g., a sterilization device, a refrigeration device, a central suction and oxygen supply system, an air conditioning device, a pharmaceutical machinery device, a blood bank device, a medical data processing device, a medical video photography device, etc.) used to assist the diagnostic device and/or the treatment device for a diagnosis and/or a treatment of the target object (e.g., the patient).

SUMMARY

One embodiment of the present disclosure may provide a method for controlling a medical device, including: obtaining information related to the medical device and/or information related to a target object; controlling the medical device based on the information related to the medical device and/or the information related to the target object.

In some embodiments, the medical device may include a scanning device. The obtaining information related to the medical device and/or information related to a target object may include: obtaining position information of one or more ionization chambers of the scanning device, the scanning device being configured to scan the target object. The controlling the medical device based on the information related to the medical device and/or the information related to the target object may include: determining a detection region of at least one ionization chamber of the one or more ionization chambers based on the position information of the one or more ionization chambers; determining projection data of a projection device, the projection data including image data corresponding to the detection region of the at least one ionization chamber; and controlling the projection device to project the projection data onto the target object.

In some embodiments, the projection data may further include image data corresponding to a region of interest to be scanned of the target object.

In some embodiments, the method may further include: obtaining a reference image of the target object, the reference image being captured by a camera after the projection device projects the projection data onto the target object to be scanned; identifying a first region in the reference image, the first region corresponding to the region of interest to be scanned of the target object; identifying a second region in the reference image, the second region corresponding to the detection region of the at least one ionization chamber projected onto the target object; and determining, based on the first region and the second region, whether the at least one ionization chamber includes one or more candidate ionization chambers, wherein detection regions of the one or more candidate ionization chambers may be covered by the region of interest to be scanned of the target object.

In some embodiments, the method may further include: in response to determining that the at least one ionization chamber does not include any candidate ionization chamber, causing a terminal device to generate prompt information; in response to determining that the at least one ionization chamber does not include any candidate ionization chamber, causing one or more reference ionization chambers of the at least one ionization chamber to be moved relative to the region of interest of the target object.

In some embodiments, the method may further include: obtaining identification information of one or more target ionization chambers selected from the at least one ionization chamber; adjusting the projection data based on the identification information, such that a first feature value of image data corresponding to detection regions of the one or more target ionization chambers in the projection data is different from a second feature value of image data corresponding to detection regions of other ionization chambers, wherein the first feature value and the second feature value may correspond to a same image feature.

In some embodiments, the obtaining information related to the medical device and/or information related to a target object may include: obtaining a virtual model of the medical device, wherein the medical device may include at least one movable first component, and accordingly the virtual model may include a second component simulating the first component, a device coordinate system in which the first component is located may have a mapping relationship with a model coordinate system in which the second component is located; and obtaining current movement information of one of the first component of the medical device and the second component of the virtual model. The controlling the medical device based on the information related to the medical device and/or the information related to the target object component may include: controlling the other one of the first component of the medical treatment device and the second component of the virtual model to perform a same movement as the one of the first component of the medical treatment device and the second component of the virtual model that obtains a movement instruction.

In some embodiments, the obtaining current movement information of one of the first component of the medical device and the second component of the virtual model may include: obtaining current movement information of the first component of the medical treatment device. Prior to obtaining the current movement information of the first component of the medical treatment device, the first component may obtain movement control information to perform a current movement.

In some embodiments, the obtaining current movement information of one of the first component of the medical device and the second component of the virtual model may include: obtaining current movement information of the second component of the virtual model. Prior to obtaining the current movement information of the second component of the virtual model, the second component may obtain movement control information to perform a current movement.

In some embodiments, the virtual model may be displayed on a display interface and real-time position information of the second component during the current movement may also be displayed on the display interface and may be updated with the movement.

In some embodiments, the obtaining information related to the medical device and/or information related to a target object may include: obtaining a model of a X-ray camera gantry based on a solid structure of the X-ray camera gantry; simulating a corresponding movement trajectory of the model by using the model of the X-ray camera gantry based on a movement trajectory of the solid structure of the X-ray camera gantry; and obtaining a movement instruction of the solid structure of a current X-ray camera gantry, the movement instruction including a target position that a component of the current X-ray camera gantry needs to move to and related movement time information. The controlling the medical device based on the information related to the medical device and/or the information related to the target object may include: causing the solid structure of the X-ray camera gantry to reach the target position based on the movement instruction; simulating, by the model of the X-ray camera gantry, a movement trajectory of the model based on the movement instruction and the movement time information synchronously; and displaying a simulation of the movement trajectory of the model on a display device.

In some embodiments, the model may be obtained according to a process including: obtaining an image of the X-ray camera gantry; and extracting a feature point of the image; obtaining the model by reconstructing the model based on the feature point.

In some embodiments, the medical device may be a medical imaging device. The obtaining information related to the medical device and/or information related to a target object may include: obtaining physical information of the target object. The controlling the medical device based on the information related to the medical device and/or the information related to the target object may include: determining abnormal physical information by analyzing the physical information; and determining a scanning parameter and/or an image processing parameter of the medical imaging device adaptively based on the abnormal physical information of the target object.

In some embodiments, the determining a scanning parameter and/or an image processing parameter of the medical imaging device adaptively based on the abnormal physical information of the target object may include: determining, based on the abnormal physical information of the target object, a disease type of the target object; determining the scanning parameter and/or the image processing parameter of the medical imaging device adaptively based on the disease type.

In some embodiments, the determining the scanning parameter and/or the image processing parameter of the medical imaging device adaptively based on the disease type may include: determining an abnormality level of the abnormal physical information; determining the scanning parameter and/or the image processing parameter of the medical imaging device adaptively based on the disease type and the abnormality level.

In some embodiments, the determining abnormal physical information by analyzing the physical information may include: inputting the physical information into a trained physical identification model; obtaining abnormal physical information output by the physical identification model; or comparing the physical information with a normal physical parameter to determine the abnormal physical information.

In some embodiments, the determining abnormal physical information by analyzing the physical information may include: comparing the physical information with standard physical information corresponding to a type of the target object to determine the abnormal physical information that does not conform to the standard physical information; wherein the type of the target object may be determined based on basic information of a human body and/or a historical medical record of the target object, and the basic information of the human body may include at least one of a gender, an age, a weight, or a height.

In some embodiments, the medical device may be a medical imaging device. The obtaining information related to the medical device and/or information related to a target object may include: obtaining a scanning parameter of the medical imaging device for the target object; obtaining abnormal physical information of the target object. The controlling the medical device based on the information related to the medical device and/or the information related to the target object may include: adjusting the scanning parameter and/or an image processing parameter of the medical imaging device adaptively based on the abnormal physical information; performing a scan on the target object to obtain a medical image, wherein the scan may be performed based on an adjusted scanning parameter, and/or the medical image may be processed based on an adjusted image processing parameter.

One embodiment of the present disclosure may provide a system for controlling a medical device, including: an information obtaining module configured to obtain information related to the medical device and/or information related to a target object; a control module configured to control the medical device based on the information related to the medical device and/or the information related to the target object.

One embodiment of the present disclosure may provide a computer-readable storage medium. The storage medium may store computer instructions. When the computer instructions are read by a computer, the computer may effectuate a method for controlling a medical device as described in any embodiment of the present disclosure.

One embodiment of the present disclosure may provide a device for controlling a medical device. The device may include at least one processor and at least one storage device. The at least one storage device may be configured to store computer instructions. The at least one processor may be configured to perform at least component of the computer instructions to effectuate a method for controlling a medical device as described in any embodiment of the present disclosure.

One embodiment of the present disclosure may provide a method for marking a detection region of an ionization chamber. The method may include: obtaining position information of one or more ionization chambers of a scanning device, the scanning device being configured to scan an object; determining a detection region of at least one ionization chamber of the one or more ionization chambers based on the position information of the one or more ionization chambers; determining projection data of a projection device, the projection data including image data corresponding to the detection region of the at least one ionization chamber; and controlling the projection device to project the projection data onto the object.

In some embodiments, the projection data may further include image data corresponding to a region of interest to be scanned of the object.

In some embodiments, the method may further include: obtaining a reference image of the object, the reference image being captured by a camera after the projection device projects the projection data onto the object to be scanned; identifying a first region in the reference image, the first region corresponding to the region of interest to be scanned of the object; identifying a second region in the reference image, the second region corresponding to the detection region of at least one ionization chamber projected onto the object; and determining, based on the first region and the second region, whether the at least one ionization chamber includes one or more candidate ionization chambers, wherein detection regions of the one or more candidate ionization chambers may be covered by the region of interest to be scanned of the object.

In some embodiments, the method may further include: in response to determining that the at least one ionization chamber does not include any candidate ionization chamber, causing a terminal device to generate prompt information.

In some embodiments, in response to determining that the at least one ionization chamber does not include any candidate ionization chamber, the method may further include: causing one or more reference ionization chambers of the at least one ionization chamber to be moved relative to the region of interest of the object.

In some embodiments, the method may further include: in response to determining that the at least one ionization chamber includes one or more candidate ionization chambers, selecting one or more target ionization chambers from the one or more candidate ionization chambers, wherein the one or more target ionization chambers may operate during a scan of the object.

In some embodiments, the method may further include: obtaining identification information of one or more target ionization chambers selected from the at least one ionization chamber; adjusting the projection data based on the identification information, such that a first feature value of the image data corresponding to detection regions of the one or more target ionization chambers in the projection data is different from a second feature value of the image data corresponding to detection regions of the other ionization chambers, wherein the first feature value and the second feature value may correspond to a same image feature.

One embodiment of the present disclosure may provide a system for marking a detection region of an ionization chamber, including: an obtaining module configured to obtain position information of one or more ionization chambers of a scanning device; a detection region determination module configured to determine a detection region of at least one ionization chamber of the one or more ionization chambers based on the position information of the one or more ionization chambers; a projection data determination module configured to determine projection data of a projection device, the projection data including image data corresponding to the detection region of the at least one ionization chamber; and a control module configured to control the projection device to project the projection data onto the object.

One embodiment of the present disclosure may provide a computer-readable storage medium. The storage medium may store computer instructions. When the computer instructions are read by a computer, the computer may effectuate a method as described in any embodiment of the present disclosure.

One embodiment of the present disclosure may provide a device for marking a detection region of an ionization chamber. The device may include a program for marking the detection region of the ionization chamber. The program may effectuate a method as described in any embodiment of the present disclosure.

One embodiment of the present disclosure may provide a method for controlling a medical treatment device. The method may include: obtaining a virtual model of the medical treatment device, wherein the medical treatment device may include at least one movable first component, and accordingly the virtual model may include a second component simulating the first component, a device coordinate system in which the first component is located may have a mapping relationship with a model coordinate system in which the second component is located; obtaining current movement information of one of the first component of the medical treatment device and the second component of the virtual model; controlling the other one of the first component of the medical treatment device and the second component of the virtual model to perform a same movement as the one of the first component of the medical treatment device and the second component of the virtual model that obtains a movement instruction.

In some embodiments, the same movement may include a synchronous movement.

In some embodiments, the medical treatment device may include an X-ray camera system.

In some embodiments, the first component may include a gantry of the X-ray camera system.

In some embodiments, the gantry may include a tube, a detector, a support element of the tube, or a support element of the detector.

In some embodiments, the obtaining current movement information of one of the first component of the medical treatment device and the second component of the virtual model may include: obtaining current movement information of the first component of the medical treatment device. Prior to obtaining the current movement information of the first component of the medical treatment device, the first component may obtain movement control information to perform a current movement.

In some embodiments, the movement control information may include a control instruction of an automatic movement of the first component or a manual operation of the first component.

In some embodiments, the obtaining current movement information of one of the first component of the medical treatment device and the second component of the virtual model may include: obtaining current movement information of the second component of the virtual model. Prior to obtaining the current movement information of the second component of the virtual model, the second component may obtain movement control information to perform a current movement.

In some embodiments, the movement control information may be input by a mouse, a keyboard, a voice, or a touch.

In some embodiments, the virtual model may be displayed on a display interface and real-time position information of the second component during the current movement may also be displayed on the display interface and may be updated with the movement.

In some embodiments, the display interface may be a display interface of a computer or a mobile terminal, or a public display interface.

In some embodiments, the virtual model may be obtained by modeling data of the gantry of the X-ray camera system.

In some embodiments, the virtual model may be obtained according to a process including: obtaining an image of the gantry of the X-ray camera system; extracting a feature point of the image; obtaining the model by reconstructing the model based on the feature point.

In some embodiments, when a component of the first component moves, the display interface may highlight a movement trajectory of a component of the second component corresponding to the component of the first component.

One embodiment of the present disclosure may provide a method for controlling a medical treatment device. The method may include: obtaining a model of an X-ray camera gantry based on a solid structure of the X-ray camera gantry; simulating a corresponding movement trajectory of the model by using the model of the X-ray camera gantry based on a movement trajectory of the solid structure of the X-ray camera gantry; obtaining a movement instruction of the solid structure of a current X-ray camera gantry, the movement instruction including a target position that a component of the current X-ray camera gantry needs to move to and related movement time information; causing the solid structure of the X-ray camera gantry to reach the target position based on the movement instruction; simulating, by the model of the X-ray camera gantry, a movement trajectory of the model based on the movement instruction and the movement time information synchronously; and displaying a simulation of the movement trajectory of the model on a display device.

In some embodiments, the model may be obtained by modeling data of the X-ray camera gantry.

In some embodiments, the model may be obtained according to a process including: obtaining an image of the X-ray camera gantry; extracting a feature point of the image; obtaining the model by reconstructing the model based on the feature point.

In some embodiments, when a component of the X-ray camera gantry moves, the displaying a simulation of the movement trajectory of the model on a display device may include: highlighting a movement trajectory of a component of the model of the X-ray camera gantry corresponding to the component of the X-ray camera gantry on the display device.

In some embodiments, the display device may be configured outside a machine room of the X-ray camera gantry, and the method may further include: obtaining interaction data by the display device; controlling a movement of the solid structure of the current X-ray camera gantry based on the interaction data.

In some embodiments, the display device may include a touch screen. The obtaining interaction data by the display device may include: controlling the model of the X-ray camera gantry by touching on the touch screen, to generate the interaction data.

One embodiment of the present disclosure may provide a system for controlling a medical treatment device. The system may include: a model obtaining module configured to obtain a virtual model of the medical treatment device, wherein the medical treatment device may include at least one movable first component, and accordingly the virtual model may include a second component simulating the first component, a device coordinate system in which the first component is located may have a mapping relationship with a model coordinate system in which the second component is located; a movement information obtaining module configured to current movement information of one of the first component of the medical treatment device and the second component of the virtual model; a movement execution module configured to control the other one of the first component of the medical treatment device and the second component of the virtual model to perform a same movement as the one of the first component of the medical treatment device and the second component of the virtual model that obtains a movement instruction.

One embodiment of the present disclosure may provide a system for controlling a medical treatment device. The system may include: a movement simulation module configured to obtain a model of a X-ray camera gantry based on a solid structure of the x-ray camera gantry, and simulate a corresponding movement trajectory of the model by using the model of the X-ray camera gantry based on a movement trajectory of the solid structure of the X-ray camera gantry; an instruction obtaining module configured to obtain a movement instruction of the solid structure of the current X-ray camera gantry, the movement instruction including a target position that a component of the current X-ray camera gantry needs to move to and related movement time information; a simulation control module configured to control the solid structure of the X-ray camera gantry to reach the target position based on the movement instruction, and stimulate, by the model of the X-ray camera gantry, a movement trajectory of the model, based on the movement instruction and movement time information; a display module configured to display a simulation of the movement trajectory of the model on a display device.

One embodiment of the present disclosure may provide a method for controlling a medical treatment device. The method may include: obtaining a movement instruction of the solid structure of the current X-ray camera gantry, the movement instruction including a target position that a component of the current X-ray camera gantry needs to move to and related movement time information; causing the solid structure of the X-ray camera gantry to reach the target position based on the movement instruction; stimulating, by the model of the X-ray camera gantry, a movement trajectory of the model based on the movement instruction and the movement time information synchronously; and displaying a simulation of the movement trajectory of the model on a display device.

One embodiment of the present disclosure may provide a system for controlling a medical treatment device. The system may include: an instruction obtaining module configured to obtain a movement instruction of the solid structure of the current X-ray camera gantry, the movement instruction including a target position that a component of the current X-ray camera gantry needs to move to and related movement time information; a simulation control module configured to control the solid structure of the X-ray camera gantry to reach the target position based on the movement instruction, and stimulate, by the model of the X-ray camera gantry, a movement trajectory of the model based on the movement instruction and the movement time information; a display module configured to display a simulation of the movement trajectory of the model on a display device.

One embodiment of the present disclosure may provide a device for controlling a medical treatment device, including: a processor, wherein the processor may be configured to perform computer instructions to implement a method as described in any embodiment of the present disclosure.

One embodiment of the present disclosure may provide a method for determining a parameter of a medical imaging device, including: obtaining physical information of a target object; determining abnormal physical information by analyzing the physical information; and determining a scanning parameter and/or an image processing parameter of the medical imaging device adaptively based on the abnormal physical information of the target object.

In some embodiments, the scanning parameter may include: a scanning voltage, a scanning current, a scanning field of view, a number of scanning layers, or a scanning layer thickness.

In some embodiments, the image processing parameter may include: an image contrast level or an image equalization level.

In some embodiments, the obtaining the physical information of the target object may be achieved by a sensor.

In some embodiments, the sensor may include a camera, a temperature sensor, a heartbeat sensor, or a respiration sensor.

In some embodiments, the determining a scanning parameter and/or an image processing parameter of the medical imaging device adaptively based on the abnormal physical information of the target object may include: determining, based on the abnormal physical of the target object, a disease type of the target object; determining the scanning parameter and/or image processing parameter of the medical imaging device adaptively based on the disease type.

In some embodiments, the determining the scanning parameter and/or image processing parameter of the medical imaging device adaptively based on the disease type may include: determining an abnormality level of the abnormal physical information; determining the scanning parameter and/or image processing parameter of the medical imaging device adaptively based on the disease type and the abnormality level.

In some embodiments, the determining abnormal physical information by analyzing the physical information may include: inputting the physical information into a trained physical identification model; obtaining the abnormal physical information output by the physical identification model, or comparing the physical information with a normal physical parameter to determine the abnormal physical information.

In some embodiments, the determining abnormal physical information by analyzing the physical information may further include: comparing the physical information with standard physical information corresponding to a type of the target object to determine abnormal physical information that does not conform to the standard physical information; wherein the type of the target object may be determined based on basic information of a human body and/or a historical medical record of the target object, and the basic information of the human body may include at least one of a gender, an age, a weight, or a height.

In some embodiments, the method may further include: determining, based on the scanning parameters, a target scanning protocol of the target object; performing a scan on the target object based on the target scanning protocol and the image processing parameter, to obtain a scanned image of the target object.

In some embodiments, the image processing parameter may be a parameter for processing a scanning algorithm of a region of interest of the target object.

One embodiment of the present disclosure may provide an imaging method for a medical imaging device, including: obtaining a scanning parameter of the medical imaging device for a target object; obtaining abnormal physical information of the target object; adjusting the scanning parameter and/or an image processing parameter of the medical imaging device adaptively based on the abnormal physical information; performing a scan on the target object to obtain a medical image, wherein the scan may be performed based on an adjusted scanning parameter, and/or the medical image may be processed based on an adjusted image processing parameter.

In some embodiments, the medical imaging device may include an X-ray camera device, an MR device, a CT device, a PET device, an ultrasound device, a DSA device, or a multi-modality imaging device.

One embodiment of the present disclosure may provide a device for determining a parameter of a medical imaging device, including: a physical information obtaining module configured to obtain physical information of a target object; an abnormal physical information determination module configured to determine abnormal physical information by analyzing the physical information; a parameter determination module configured to determine a scanning parameter and/or an image processing parameter of the medical imaging device adaptively based on the abnormal physical information of the target object.

One embodiment of the present disclosure may provide a medical imaging device including: an imaging component configured to scan a target object to obtain a medical image; a sensor configured to obtain abnormal physical information of the target object; a controller, coupled to the imaging component and the sensor, and configured to adjust a scanning parameter of the imaging component adaptively based on the abnormal physical information, and/or adjust an image processing parameter of the medical image adaptively based on the abnormal physical information.

In some embodiments, the sensor may include a camera, a temperature sensor, a heartbeat or a pulse sensor, or a respiration sensor.

One embodiment of the present disclosure may provide a device. The device may include: one or more processors; a storage device configured to store one or more programs. When the one or more programs are executed by the one or more processors, the one or more processors may implement a method for determining a parameter of a medical imaging device, and/or an imaging method of a medical imaging device as described in any embodiment of the present disclosure.

One embodiment of the present disclosure may provide a storage medium including computer executable instructions. When executed by a computer processor, the computer-executable instructions may be used to execute a method for determining a parameter of a medical imaging device, and/or an imaging method of a medical imaging device as described in any embodiment of the present disclosure.

BRIEF DESCRIPTION OF THE DRAWINGS

The present disclosure will be further described by exemplary embodiments. These exemplary embodiments will be described in detail by way of the accompanying drawings. The accompanying drawings are not drawn to scale. These embodiments are non-limiting exemplary embodiments in which like reference numerals represent similar structures, wherein:

FIG. 5 is a flowchart illustrating an exemplary process for adjusting projection data according to some embodiments of the present disclosure;

FIG. 6 is a schematic block diagram illustrating a system for marking a detection region of an ionization chamber according to some embodiments of the present disclosure;

FIG. 7 is a flowchart illustrating an exemplary process for controlling a medical treatment device according to some embodiments of the present disclosure;

FIG. 9 is a flowchart illustrating an exemplary process for controlling a medical treatment device according to some embodiments of the present disclosure;

DETAILED DESCRIPTION

Figure 1:
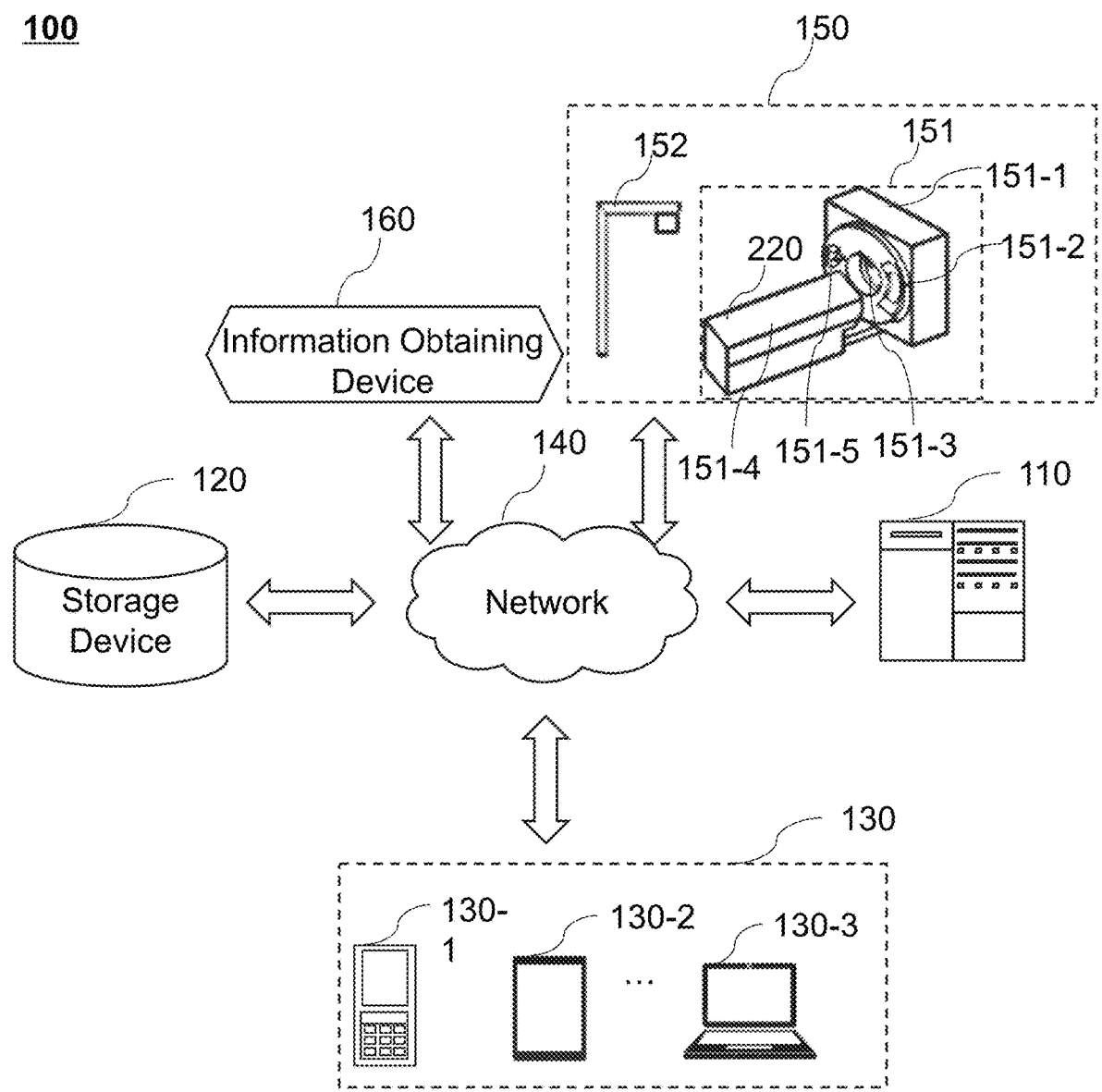
FIG. 1 is a schematic diagram illustrating an application scenario of a medical device control system according to some embodiments of the present disclosure.

The technical schemes of the present disclosure embodiments will be more clearly described below, and the accompanying drawings need to be configured in the description of the embodiments will be briefly described below. Obviously, the drawings in the following description are merely some examples or embodiments of the present disclosure, and will be applied to other similar scenarios according to these accompanying drawings without paying creative labor. Unless obviously obtained from the context or the context illustrates otherwise, the same reference numerals in the drawings refers to the same structure or operation.

It should be It should be understood that the "system," "device," "unit" and/or "module" used herein is a method for distinguishing different components, elements, parts, sections or assemblies of different levels. However, the terms may be displaced by another expression if they achieve the same purpose.

As shown in the present disclosure and the claims, unless the context clearly prompts the exception, "a," "one," and/or "the" is not specifically singular, and the plural may be included. It will be further understood that the terms "comprise," "comprises," and/or "comprising," "include," "includes," and/or "including," when used in present disclosure, specify the presence of stated features, integers, steps, operations, elements, and/or components, but do not preclude the presence or addition of one or more other features, integers, steps, operations, elements, components, and/or groups thereof.

While the present disclosure makes various references to certain modules or units in the system according to embodiments of the present disclosure, however, any number of different modules or units may be used and run on the client and/or the server. The modules described are illustrative only, and different modules may be used for different aspects of the described systems and methods.

The flowcharts are used in the present disclosure to illustrate the operations performed by the system according to embodiments of the present disclosure. It should be understood that the preceding or following operations are not necessarily performed in precise order. Instead, the individual steps may be processed in reverse order or simultaneously. It is also possible to add other operations to these processes or to remove a step or steps of operations from these processes.

In the present disclosure, the term "and/or" may include any one or more of the relevant listed entries or any combinations thereof. The term "image" is used in the present disclosure to refer collectively to image data (e.g., scanned data, projection data) and/or images in various forms, including a two-dimensional (2D) image, a three-dimensional (3D) images, a four-dimensional (4D) image, etc.

The present disclosure provides systems and methods for controlling a medical device. In some embodiments, the medical device may include a digital subtraction angiography (DSA), a digital breast tomosynthesis (DBT), a cone beam CT (CBCT), a direct digital radiography (DR), an X-ray computed tomography (CT), a mobile C-arm, etc. In some embodiments, the systems and methods for controlling the medical device provided in embodiments of the present disclosure may be used to control a medical device and may also be used to control a component of the medical device. For example, the systems and methods provided in embodiments of the present disclosure may be used to control the components such as a tube, an ionization chamber, a detector, a scanning bed, etc.

In some embodiments, the systems and methods for controlling the medical device may be applied to mark a detection region of an ionization chamber. During a clinical use, it is necessary to make an object to be scanned or a region of interest (ROI) correctly cover the detection region of the ionization chamber, otherwise it may lead to a low exposure dose and affect an image quality. In an actual operation, an operator cannot obtain an accurate position of the detection region of the ionization chamber due to a lack of a position marking of the detection region of the ionization chamber or the occlusion of the object, and thus cannot accurately determine whether the object to be scanned or the region of interest covers the detection region of the ionization chamber, which may lead to a low image quality. The systems and methods for marking the detection region of the ionization chamber provided in the present disclosure can help the operator obtain the accurate position of the detection region of the ionization chamber, so that the operator can accurately determine whether the object to be scanned or the region of interest covers the detection region of the ionization chamber, which can improve the quality of a scanned image and reduce the time and effort required by the operator.

In some embodiments, the systems and methods for controlling the medical device may also be applied to a DSA or a DR device. In the case of the DSA, for example, when the DSA is performing a camera task, the operator cannot observe a specific movement position of each joint or structure of the DSA gantry in real time due to the limitations of its working environment, and the systems and methods for controlling the medical device may synchronize the movement of the DSA gantry to a visual display device. The movement of the DSA may be displayed synchronously through a model, which may be convenient for the operator to observe and monitor the movement of the DSA gantry and the movement parameter. The systems and methods for controlling the medical device may also control the movement of the DSA gantry by controlling a movement of the model in the display device, which may further improve the interactivity of the DSA with the user, and facilitate the operator to use.

In some embodiments, the systems and methods for controlling the medical device may be applied to a medical imaging device. In particular, the medical imaging device may include at least one of an X-ray camera device, an MR device, a CT device, a PET device, an ultrasound device, a DSA device, and a multi-modality imaging device. By obtaining physical information of a target object, analyzing the physical information, determining abnormal physical information, and determining a scanning parameter and/or an image processing parameter of the medical imaging device based on the abnormal physical information of the target object, the scanning parameter of the medical imaging device may be determined in time based on the physical information of the target object, to achieve the purpose of improving a diagnostic efficiency. At the same time, it can avoid the problem that a doctor needs to constantly adjust the scanning parameter and/or the image processing parameter, resulting in poor image quality, repeated scanning, low efficiency, and affect the diagnosis, and can avoid the problem that the target object receives too much radiation dose.

It should be understood that the application scenarios of the systems and methods for controlling the medical device are only some examples or embodiments of the present disclosure. The present disclosure may be applied to other similar scenarios by a person of ordinary skill in the art, without creative effort, in accordance with these accompanying drawings. For example, the methods and systems of the embodiments of the present disclosure may be applied to a robotic arm or a robot used in industry.

FIG. 1 is a schematic diagram illustrating an application scenario of a medical device control system according to some embodiments of the present disclosure. As shown in FIG. 1, the medical device control system 100 may include a processing device 110, a storage device 120, one or more terminals 130, a network 140, a medical device 150, and an information obtaining device 160. In some embodiments, the processing device 110, the storage device 120, the terminal 130, the medical device 150, and/or the information obtaining device 160 may be connected with each other and/or communicate via a wireless connection, a wired connection, or a combination thereof. The connections between the components of the system 100 may be variable. Merely by way of example, the information obtaining device 160 may be connected to the processing device 110 via the network 140 or directly. As another example, the storage device 120 may be connected to the processing device 110 via the network 140 or directly.

The processing device 110 may process data and/or information obtained from the storage device 120 and/or the terminal 130. For example, the processing device 110 may cause a scanning device 151 to obtain image data from the scanning device 151. As another example, the processing device 110 may obtain a user instruction from the terminal 130. As another example, the processing device 110 may obtain information related to the medical device 150 and/or the target object from the information obtaining device 160.

The processing device 110 may also send a control instruction to one or more components (e.g., the storage device 120, the terminal 130, the medical device 150, and/or the information obtaining device 160) of the system 100. For example, the processing device 110 may send the control instruction to the medical device 150 to move a movable component (e.g., an ionization chamber, a detector, etc.) of the medical device 150 to a specific position. As another example, the processing device 110 may send the control instruction to the terminal 130 to cause the terminal 130 to display the image data on a display interface thereof. As another example, the processing device 110 may determine a detection region of an ionization chamber of the medical device 150 and accordingly control a projection device to project the detection region of the ionization chamber of the medical device 150 onto an object (i.e., the target object). As another example, the information obtaining device 160 may obtain current movement information of one of a virtual model of the medical device 150, a first component of the medical device 150, and a second component of the virtual model, wherein the second component of the virtual model may be used to simulate the first component of the medical device 150, a device coordinate system in which the first component is located may have a mapping relationship with a model coordinate system in which the second component is located. The processing device 110 may control the other one of the first component of the medical treatment device and the second component of the virtual model to perform a same movement as the one of the first component of the medical treatment device and the second component of the virtual model that obtains a movement instruction. As another example, the information obtaining device 160 may obtain physical information of the target object. The processing device 110 may analyze the physical information, determine abnormal physical information, and determine a scanning parameter and/or an image processing parameter of the medical device 150 adaptably based on the abnormal physical information of the target object.

In some embodiments, the processing device 110 may be a single server or a server group. The server group may be centralized or distributed. In some embodiments, the processing device 110 may be local or remote to the system 100. For example, the processing device 110 may access information and/or data from the scanning device 151, the storage device 120, the terminal 130, the medical device 150, and/or the information obtaining device 160 via the network 140. As another example, the processing device 110 may directly connect to the storage device 120, the terminal 130, the medical device 150, and/or the information obtaining device 160 to access the information and/or the data. In some embodiments, the processing device 110 may be implemented on a cloud platform. For example, the cloud platform may include a private cloud, a public cloud, a hybrid cloud, a community cloud, a distributed cloud, an inter-cloud, a multi-cloud, or any combination thereof.

In some embodiments, the processing device 110 may include one or more processors (e.g., a single-chip processor or a multi-chip processor). Merely by way of example, the processing device 110 may include a central processing unit (CPU), a specialized integrated circuit (ASIC), a specialized instruction set processor (ASIP), an image processing unit (GPU), a physical computing processing unit (PPU), a digital signal processor (DSP), a field programmable gate array (FPGA), a programmable logic device (PLD), a controller microcontroller unit, a reduced instruction set computer (RISC), a microprocessor, or the like, or any combination thereof.

The storage device 120 may store data, instructions, and/or any other information. In some embodiments, the storage device 120 may store data obtained from the processing device 110, the terminal 130, the medical device 150, and/or the information obtaining device 160. In some embodiments, the storage device 120 may store data and/or instructions that may be performed by the processing device 110 or used to perform exemplary processes described in the present disclosure. In some embodiments, the storage device 120 may include a mass storage device, a removable storage device, a volatile read-write memory, a read-only memory (ROM), or the like, or any combination thereof. Exemplary mass storage devices may include a disk, an optical disk, a solid state drive, etc. Exemplary removable storage devices may include a flash drive, a floppy disk, an optical disk, a memory card, a zip disk, a magnetic tape, etc. Exemplary volatile read-write memories may include a random access memory (RAM). Exemplary RAMs may include a dynamic random access memory (DRAM), a double data rate synchronous dynamic access memory (DDR SDRAM), a static random access memory (SRAM), a thyristor random access memory (T-RAM), a zero capacitance random access memory (Z-RAM), etc. Exemplary ROMs may include a mask-mode read-only memory (MROM), a programmable read-only memory (PROM), an erasable programmable read-only memory (EPROM), an electrically erasable read-only memory (EEPROM), a compact disc read-only memory (CD-ROM), a digital universal CD-ROM, etc. In some embodiments, the storage device 120 may be implemented on the cloud platform described elsewhere in the present disclosure.

In some embodiments, the storage device 120 may be connected to the network 140 to communicate with one or more other components (e.g., the terminal 130, the medical device 150, and/or the information obtaining device 160) of the system 100. One or more components of the system 100 may access data or instructions stored in the storage device 120 via the network 140. In some embodiments, the storage device 120 may be part of the processing device 110.

The terminal 130 may enable an interaction between a user and one or more components of the system 100. For example, the terminal 130 may display image data, e.g., image data of a detection region of an ionization chamber, image data of a region of interest of an object to be scanned (i.e., the target object), etc. The user may issue an instruction via the terminal 130 based on the image data, for example, an instruction to the medical device 150 to specify a selected target ionization chamber, an instruction to the medical device 150 to start an imaging and/or a scan, and as another example, an instruction to the storage device 120 to store the image data, etc. In some embodiments, the terminal 130 may include a mobile device 130-1, a tablet computer 130-2, a laptop computer 130-3, or the like, or any combination thereof. For example, the mobile device 130-1 may include a cell phone, a personal digital assistant (PDA), a gaming device, a navigation device, a point-of-sale (POS) device, a laptop computer, a tablet computer, a desktop computer, or the like, or any combination thereof. In some embodiments, the terminal 130 may include an input device, an output device, etc. In some embodiments, the terminal 130 may be part of the processing device 110.

The network 140 may include any suitable network that may facilitate an exchange of the information and/or data of the system 100. In some embodiments, the one or more components (e.g., the processing device 110, the storage device 120, the terminal 130, the medical device 150, and/or the information obtaining device 160) of the system 100 may communicate information and/or data with one or more other components of the system 100 via the network 140. For example, the processing device 110 may obtain medical image data from the medical device 150 via the network 140. As another example, the processing device 110 may obtain the user instruction from the terminal 130 via the network 140. As another example, the projection device 152 may obtain projection data from the scanning device 151, the processing device 110, the storage device 120, and/or the information obtaining device 160 via the network 140.

The network 140 may be or include a public network (e.g., the Internet), a private network (e.g., a local area network (LAN)), a wired network, a wireless network (e.g., an 802.11 network, a Wi-Fi network), a gantry relay network, a virtual private network (VPN), a satellite network, a telephone network, a router, a hub, a switch, a server computer, or the like, or any combination thereof. For example, the network 140 may include a cable network, a wired network, a fiber optic network, a telecommunications network, the Intranet, a wireless local area network (WLAN), a metropolitan area network (MAN), a public switched telephone network (PSTN), a Bluetooth network, a ZigBee network, a near field communication (NFC) network, or the like, or any combination thereof. In some embodiments, the network 140 may include one or more network access points. For example, the network 140 may include a wired and/or wireless network access point such as a base station and/or an Internet exchange point, through which one or more components of the system 100 may connect to the network 140 to exchange data and/or information.

The medical device 150 may be an automated device that performs a medical treatment or a research task. The medical treatment or the research task may include, but are not limited to, a medical camera task, a surgical task, a rehabilitation treatment task, or the like. In some embodiments, the medical device 150 may include a scanning device 151 and a projection device 152. The scanning device 151 may generate or provide image data related to an object (i.e., a target object) by scanning the object (i.e., the target object). In some embodiments, the object (i.e., the target object) may include a biological object and/or a non-biological object. For example, the object (i.e., the target object) may include a particular portion of a body, such as the head, the chest, the abdomen, or the like, or any combination thereof. As another example, the object (i.e., the target object) may be an artificial object of animate or inanimate organic and/or inorganic material. In some embodiments, the scanning device 151 may be a non-invasive biomedical imaging device for a disease diagnosis or research purpose. The scanning device 151 may include a single modality scanner and/or a multi-modality scanner. The single modality scanner may include, for example, an X-ray scanner, a computed tomography (CT) scanner, a digital radiography (DR) scanner (e.g., a mobile digital radiography), a digital subtraction angiography (DSA) scanner, a dynamic spatial reconstruction (DSR) scanner, an X-ray microscope scanner, or the like, or any combination thereof. For example, the X-ray imaging device may include an X-ray source and a detector. The X-ray source may be configured to emit X-rays to the object to be scanned. The detector may be configured to detect the X-rays passing through the object. In some embodiments, the X-ray imaging device may be, for example, a C-shaped X-ray imaging device, a vertical X-ray imaging device, a suspended X-ray imaging device, or the like. The multi-modality scanner may include, for example, an X-ray imaging-magnetic resonance imaging (X-ray-MRI) scanner, a positron emission tomography-X-ray imaging (PET-X-ray) scanner, a positron emission tomography-computed tomography (PET-CT) scanner, a digital subtraction angiography-magnetic resonance imaging (DSA-MRI) scanner, etc.

The scanners provided above are for illustrative purposes only and are not intended to limit the scope of the present disclosure. As used herein, the term "imaging modality" or "modality" broadly refers to an imaging method or technique for collecting, generating, processing, and/or analyzing imaging information of an object.

For purposes of illustration, the present disclosure primarily describes systems and methods relating to X-ray imaging systems. It should be noted that the X-ray imaging systems illustrated below are provided as examples only and are not intended to limit the scope of the present disclosure. The systems and methods disclosed herein may be any other imaging system.

In some embodiments, the scanning device 151 may include a gantry 151-1, a detector 151-2, a detection region 151-3, a scanning table 151-4, and a radiation source 151-5. The gantry 151-1 may support the detector 151-2 and the radiation source 151-5. The object may be disposed on the scanning table 151-4 and then be moved to the detection region 151-3 for scanning. The radiation source 151-5 may emit radioactive rays to the object. The radioactive rays may include particle rays, photon rays, or the like, or any combinations thereof. In some embodiments, the radioactive rays may include at least two radioactive particles (e.g., neutrons, protons, electrons, p mesons, heavy ions), at least two radioactive photons (e.g., X-rays, y-rays, ultraviolet rays, lasers), or the like, or any combinations thereof. The detector 151-2 may detect the radiation emitted from the detection region 151-3. In some embodiments, the detector 151-2 may include at least two detector units. The detector units may be a single-row detector or a multi-row detector.

The projection device 152 may include any suitable device capable of projecting image data. For example, the projection device 152 may be a cathode ray tube (CRT) projector, a liquid crystal display (LCD) projector, a digital light processor (DLP) projector, a digital light path vacuum tube (DLV) projector, or other device capable of projecting the image data.

Before the scanning device 151 performs a scan of the object, the projection device 152 may be configured to project projection data to be projected onto the object to be scanned. In some embodiments, the projection data may include image data corresponding to a detection region of at least one ionization chamber of one or more ionization chambers. For example, prior to the scan, the projection device 152 may obtain the image data of the detection region of the at least one of the one or more ionization chambers, and project the image data onto the object to be scanned. In some embodiments, the projection data may also include image data corresponding to a region of interest (ROI) of the object to be scanned.

In some embodiments, the projection device 152 may be a device independent of the scanning device 151, as shown in FIG. 1. For example, the projection device 152 may be a projector mounted on a ceiling of an examination room, and the scanning device 151 may be located in the examination room. Alternatively, the projection device 152 may be integrated into or mounted on the scanning device 151 (e.g., the gantry 111).

In some embodiments, the medical device 150 may include a medical imaging device. The medical imaging device may include an X-ray camera device, an MR (magnetic resonance) device, a CT (computed tomography) device, a PET (positron emission computed tomography) device, an ultrasound device, a DSA (digital subtraction angiography) device, or a multi-modality imaging device, etc.

In some embodiments, the medical device 150 may also include a medical treatment device. The medical treatment device may include, but is not limited to, a digital subtraction angiography (DSA), a digital breast tomosynthesis (DBT), a cone beam CT (CBCT), a digital radiography system (DR), an X-ray computed tomography (CT), a mobile C-arm, or the like.

In some embodiments, the information obtaining device 160 may be used to obtain information related to the medical device 150 and/or information related to the target object. In some embodiments, the target object may be an object undergoing a non-invasive imaging for a disease diagnosis or research purpose, for example, a human or an animal, etc. In some embodiments, the information related to the medical device 150 and/or the information related to the target object obtained by the information obtaining device 160 may include information related to positions of one or more ionization chambers of the scanning device 151. In other embodiments, the information related to the medical device 150 and/or the information related to the target object obtained by the information obtaining device 160 may include a virtual model of the medical device 150, wherein the medical device 150 may include at least one movable first component, and accordingly, the virtual model may include a second component that simulates the first component. A device coordinate system in which the first component is located may have a mapping relationship with a model coordinate system in which the second component is located. The information related to the medical device 150 and/or the information related to the target object obtained by the information obtaining device 160 may also include current movement information of one of the first component of the medical device and the second component of the virtual model. In other embodiments, the information related to the medical device 150 and/or the information related to the target object obtained by the information obtaining device 160 may include physical information of the target object, wherein the physical information may be basic physical information of the target object, such as, but not limited to, body temperature information, blood pressure information, blood lipid information, respiration information, pulse information, eye physical information, hand physical information, leg physical information, or head physical information of the target object.

In some embodiments, the information obtaining device 160 may include a sensor for obtaining feature information of the target object. The sensor may include a position sensor, an image sensor, a temperature sensor, a heartbeat sensor, or a breathing sensor, etc. In some embodiments, the information obtaining device 160 may be part of the processing device 110.

In some embodiments, the system 100 may also include an image capture device (e.g., a camera or a video camera) for capturing image data of an object. In some embodiments, the image capture device may capture the projection data projected on the object while capturing the image data of the object. In some embodiments, the image capture device may be one of the information obtaining devices 160.

The image capture device may be and/or include any suitable device capable of capturing the image data of the object. For example, the image capture device may include a camera (e.g., a digital camera, an analog camera, etc.), a red, green, and blue (RGB) sensor, an RGB depth (RGB-D) sensor, or other device that can capture color image data of the object.

In some embodiments, the image capture device may be a device independent of the scanning device 151. Alternatively, the image capture device may be integrated into or mounted on the scanning device 151 (e.g., the gantry 111). In some embodiments, the image data obtained by the image capture device may be transmitted to the processing device 110 for further analysis. Additionally or alternatively, the image data obtained by the image capture device may be sent to a terminal device (e.g., the terminal 130) for display and/or a storage device (e.g., the storage device 120) for storage.

In some embodiments, the image capture device may capture the image data of the object continuously or intermittently (e.g., periodically) before, during, and/or after a scan of the object that is performed by the scanning device 151.

In some embodiments, the obtaining of the image data by the image capture device, the transmission of the captured image data to the processing device 110, and the analysis of the image data may be performed substantially in real time such that the image data may provide information indicative of a substantially real-time state of the object.

It should be noted that the above description of the system 100 is intended to be illustrative and not to limit the scope of the present disclosure. Many alternatives, modifications and variations will be apparent to those of ordinary skill in the art. The features, structures, methods, and other characteristics of the exemplary embodiments described herein may be combined in various ways to obtain additional and/or alternative exemplary embodiments. For example, the system 100 may include one or more additional components. Additionally or alternatively, one or more components of the system 100, such as the image capture device, may be omitted. As another example, two or more components of the system 100 may be integrated into a single component. Merely by way of example, the processing device 110 (or a portion thereof) may be integrated into the scanning device 151.

In some embodiments, the medical device control system 100 (e.g., the processing device 110) may be used to perform a method for marking a detection region of an ionization chamber, a method for controlling a medical treatment device, and/or a method for determining a parameter of a medical imaging device, an imaging method. In some embodiments, the method for marking the detection region of the ionization chamber, the method for controlling the medical treatment device, the method for determining the parameter of the medical imaging device, and the imaging method may be implemented separately or in combination with each other.

Figure 2:
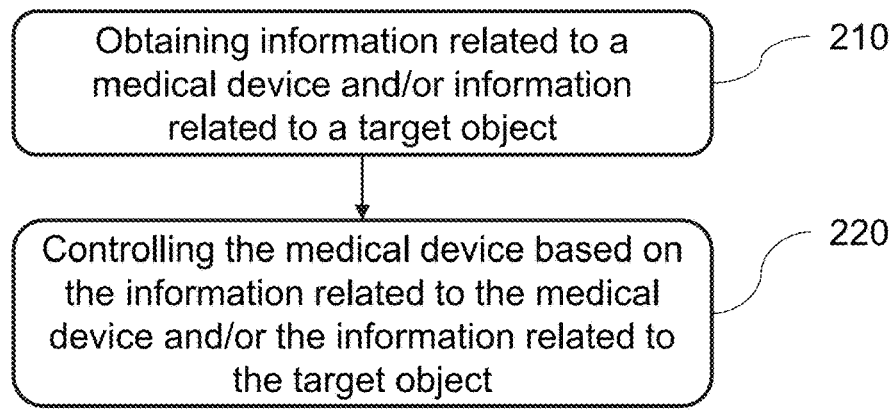
FIG. 2 is a flowchart illustrating an exemplary process for controlling a medical device according to some embodiments of the present disclosure.

FIG. 2 is a flowchart illustrating an exemplary process for controlling a medical device according to some embodiments of the present disclosure. Specifically, the process 200 may be executed by the processing device 110. For example, the process 200 may be stored in a storage device (e.g., the storage device 120) in a form of a program or instructions, and when the system 100 executes the program or the instructions, the process 200 for marking a detection region of an ionization chamber may be implemented. As shown in FIG. 2, the process 200 may include the following operations.

In operation 210, information related to a medical device and/or information related to a target object may be obtained.

The medical device may be an automated device that performs a medical diagnosis and treatment task. The medical diagnosis and treatment task may include, but are not limited to, a medical photography task, a surgical task, a rehabilitation treatment task, or the like. In some embodiments, the medical device may include a scanning device and a projection device. The scanning device may include a single-modality scanner (e.g., an X-ray scanner, a computed tomography (CT) scanner, a digital radiography (DR) scanner (e.g., a mobile digital radiography), a digital subtraction angiography (DSA) scanner, a dynamic spatial reconstruction (DSR) scanner X-ray microscope scanner, etc.) and/or a multi-modality scanner (e.g., X-ray imaging-magnetic resonance imaging (X-ray-MRI) scanner, a positron emission tomography-X-ray imaging (PET-X-ray) scanner, a positron emission tomography-computed tomography (PET-CT) scanner, a digital subtraction angiography-magnetic resonance imaging (DSA-MRI) scanner, etc.). The projection device may be a device capable of projecting image data, for example, a cathode ray tube (CRT) projector, a liquid crystal display (LCD) projector, a digital light processor (DLP) projector, a digital light path vacuum tube (DLV) projector, or other devices that can project the image data. In some embodiments, the medical device may include a medical imaging device, for example, an X-ray camera device, an MR (magnetic resonance) device, a CT (computed tomography) device, a PET (positron emission computed tomography) device, an ultrasound device, a DSA (digital subtraction angiography) device, or a multi-modality imaging device, etc. In some embodiments, the medical device may also include a medical treatment device, such as a digital subtraction angiography (DSA) machine, a digital breast tomosynthesis (DBT), a cone beam CT (CBCT), a direct digital X-ray (DR), an X-ray computed tomography (CT), a mobile C-arm, etc. More descriptions of the medical device may be found in FIG. 1 and descriptions thereof.

In some embodiments, the information related to the medical device may include information related to an imaging, for example, position information of one or more ionization chambers, wherein the position information of the ionization chamber may include position information of the ionization chamber relative to one or more components (e.g., a detector) of the scanning device and/or the position of the ionization chamber in a 3D coordinate system. In some embodiments, the position of the ionization chamber relative to a detector (e.g., a flat panel detector) of the scanning device may be fixed. The operator and/or the scanning device may adjust the position of the detector based on the position of the ROI of the object prior to the scan. The processing device 110 may obtain the position of the detector of the scanning device in the examination room and a fixed position of the ionization chamber relative to the detector of the scanning device, to determine the position information of the ionization chamber in the examination room. In some embodiments, the position of the ionization chamber relative to the detector of the scanning device may be adjustable. For example, the ionization chamber may be mounted within a removable cassette. A position sensor may be mounted in the cassette and/or other components of the scanning device. The processing device 110 may obtain the data detected by the position sensor to determine the position of the ionization chamber. More descriptions of the position information of the ionization chamber may be found in FIG. 3 and descriptions thereof.

In some embodiments, the information related to the medical device may also include a virtual model of the medical device and current movement information. The medical device may include at least one first component that is movable. Accordingly, the virtual model may include a second component simulating the first component. A device coordinate system in which the first component is located may have a mapping relationship with a model coordinate system in which the second component is located. The current movement information may be movement information of at least one of the first component of the medical device and the second component of the virtual model. In some embodiments, the virtual model may be obtained by modeling data of the medical treatment device, and the movement information may be obtained based on movement control information. More descriptions of the virtual model and/or the current movement information may be found in FIG. 7 and descriptions thereof.

The target object may be an object for a non-invasive imaging for a disease diagnosis or research purpose. In some embodiments, the target object may include a biological object and/or a non-biological object. For example, the object may include a specific portion of a body, such as the head, the chest, the abdomen, or the like, or any combination thereof. As another example, the object may be an artificial object of animate or inanimate organic and/or inorganic material.

In some embodiments, the information related to the target object may include position information, physical information, etc., of the target object. In some embodiments, the physical information may be basic physical information of the target object, such as, but not limited to, body temperature information, blood pressure information, blood lipid information, respiration information, pulse information, eye physical information, hand physical information, leg physical information, head physical information, etc., of the target object. In some embodiments, the information related to the target object may be obtained via a sensor. The sensor may include a position sensor, a camera, a temperature sensor, a heartbeat sensor, a respiration sensor, etc. More descriptions of the physical information of the target object may be found in FIG. 13 and descriptions thereof.

In operation 220, the medical device may be controlled based on the information related to the medical device and/or the information related to the target object.

In some embodiments, the processing device 110 may control the medical device to project onto the target object based on the information related to the medical device. Further, the processing device 110 may determine projection data based on the position information of the one or more ionization chambers, and control the projection device to project the projection data onto the target object. For example, the processing device 110 may determine a detection region of at least one ionization chamber of the one or more ionization chambers based on the position information of the one or more ionization chambers, determine the projection data of the projection device, the projection data including image data corresponding to the detection region of the at least one ionization chamber, and control the projection device to project the projection data onto the object. More descriptions for controlling the projection of the medical device on the target object may be found in FIG. 3 and descriptions thereof.

In some embodiments, the processing device 110 may control a movement of the medical device based on the information related to the medical device. Further, the processing device 110 may control the movement of the medical device based on the virtual model of the medical device. For example, the processing device 110 may obtain current movement information of one of the first component of the medical treatment device and the second component of the virtual model, and control the other one of the first component of the medical treatment device and the second component of the virtual model to perform a same movement as the one of the first component of the medical treatment device and the second component of the virtual model that obtains a movement instruction. More descriptions for controlling the movement of the medical device may be found in FIG. 7 and descriptions thereof.

In some embodiments, the processing device 110 may control the medical device to scan the target object based on the information related to the target object. Further, the processing device 110 may control the medical device to scan the target object based on the physical information of the target object. For example, the processing device 110 may analyze the physical information of the target object, determine abnormal physical information, and determine a scanning parameter and/or an image processing parameter of the medical imaging device adaptably based on the abnormal physical information of the target object. More information for controlling the movement of the medical device may be found in FIG. 13 and descriptions thereof.

In some embodiments, the processing device 100 may control the medical device based on the information related to the medical device and the information related to the target object. For example, the processing device 100 may control the medical device to scan the target object based on the information related to the medical device and the information related to the target object. In some embodiments, before the scan of the target object, the processing device 110 may analyze the physical information of the target object, determine the abnormal physical information, and determine the scanning parameter and/or the image processing parameter of the medical device adaptably based on the abnormal physical information of the target object. At the same time, before the scan of the target object, the processing device 110 may determine the detection region of the at least one ionization chamber of the one or more ionization chambers based on the position information of the one or more ionization chambers, determine the projection data for the projection device, and then control the projection device to project the projection data onto the target object. Further, the processing device 110 may determine one or more target ionization chambers based on a projection result of the projection data of the detection region of the at least one ionization chamber (e.g., image data of the detection region of the ionization chamber that is projected onto a body surface of the target object, and the chamber may be labeled as a candidate ionization chamber). The processing device 110 may scan the target object in the one or more target ionization chambers based on the determined scanning parameter of the medical device, and/or the processing device 110 may process a scanned image based on the determined image processing parameter of the medical device after obtaining the scanned image. In some embodiments, before the scan of the target object, in response to determining that the at least one ionization chamber does not include any candidate ionization chamber, the processing device 110 may control the scanning table 151-4 to move the target object into the detection region of the at least one ionization chamber for scanning based on the position information of the target object. More descriptions of the candidate ionization chamber and the target ionization chamber may be found in FIG. 7 and descriptions thereof.

The automatic exposure control (AEC) technology may use the ionization chambers to detect the amount of radiation after passing through the scanned object, so as to control the exposure time of the X-ray device and the total amount of X-rays, which can make the X-ray images of different portions and different patients have the same level of light sensitivity, and avoid the phenomenon that the dose difference between captured images is too large and the image quality is uneven. In the clinical use, it is necessary to make the object to be scanned or the region of interest (ROI) to be scanned covers the detection region of the ionization chamber correctly, otherwise it may lead to a low exposure dose and reduce the image quality. In a traditional way, the detection region of the ionization chamber may be generally marked on a surface of the device using a marking box or a marking line. In practice, since the position marking of the detection region of the ionization chamber may be obscured by the human body or clothing easily, or a movable object surface (e.g., a movable bed surface of an examination bed) cannot mark the detection region of the ionization chamber, which may make it difficult for the operator to obtain the accurate position of the detection region of the ionization chamber, and thus cannot accurately determine whether the object to be scanned or the region of interest covers the detection region of the ionization chamber. Therefore, it is necessary to provide methods and systems for marking the detection region of the ionization chamber.

Figure 3:
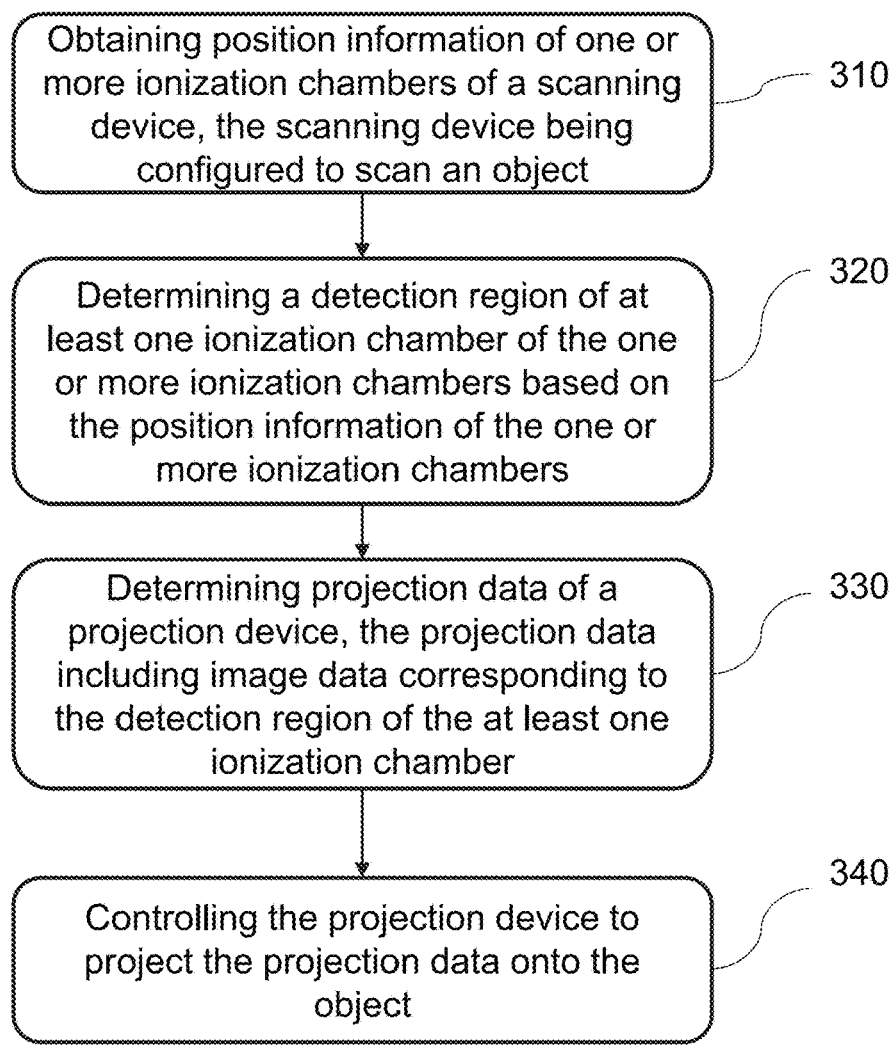
FIG. 3 is a flowchart illustrating an exemplary process for marking a detection region of an ionization chamber according to some embodiments of the present disclosure.

FIG. 3 is a flowchart illustrating an exemplary process for marking a detection region of an ionization chamber according to some embodiments of the present disclosure. Specifically, the process 300 may be executed by the processing device 110. For example, the process 300 may be stored in a storage device (e.g., the storage device 120) in a form of a program or instructions, and when the system 100 executes the program or the instructions, the process 300 for marking a detection region of an ionization chamber may be implemented. As shown in FIG. 3, the process 300 may include the following operations.

In operation 310, position information of one or more ionization chambers of a scanning device may be obtained. The scanning device may be configured to scan an object.

Specifically, the operation may be performed by an obtaining module 610.

In some embodiments, the scanning device (e.g., the scanning device 151) may be used to scan the object (i.e., a target object), such as a patient, located in an examination room. Merely by way of example, the scanning device may be a medical imaging device, such as a suspended X-ray imaging device, a vertical X-ray imaging device, a digital radiography (DR) device (e.g., a mobile digital X-ray medical imaging device), or the like, as described elsewhere in the present disclosure. For example, the scanning device may be the vertical X-ray imaging device. When a scan is performed, rays emitted from an X-ray source may pass through a region of interest (ROI) of a standing patient, and an image receiver of the scanning device may detect an intensity of the X-rays passing through the ROI of the patient. The ROI may include one or more body portions (e.g., tissue, an organ) of the object to be scanned.

In some embodiments, the processing device 110 may determine a region of interest (ROI) of a target object (e.g., a patient) based on physical information of the target object (e.g., the patient). Further, the processing device 110 may determine abnormal physical information based on the physical information of the target object (e.g., the patient), determine a disease type of the target object based on the abnormal physical information of the target object, and determine the region of interest (ROI) of the target object based on the disease type of the target object. For example, if the body temperature of the target object is relatively high, the lungs of the target object may have abnormalities, and the lungs may be determined as the region of interest (ROI) of the target object.

The ionization chamber of the scanning device may be configured to detect a radiation amount reaching a detector of the scanning device (e.g., a radiation amount in a detection region of the ionization chamber over a certain time period). The ionization chamber may typically be disposed between the detector and the object to be scanned. In some embodiments, the ionization chamber may include a solid ionization chamber, a liquid ionization chamber, an air ionization chamber, and various other ionization chambers suitable for a medical imaging process, which is not limited in the present disclosure. In some embodiments, one or more target ionization chambers may be selected from multiple ionization chambers (as described in connection with operation 460 in FIG. 4). The one or more target ionization chambers may be activated when scanning the target object, while the other chambers (if any) may be turned off when scanning the target object. In some embodiments, the automatic exposure control (AEC) method may be implemented when scanning the target object. A radiation controller (e.g., a component of the scanning device 151 or a control module 640) may cause the radiation source of the scanning device to stop scanning when a radiation accumulation detected in the one or more target ionization chambers exceeds a threshold.

In some embodiments, the position information of the ionization chamber in the examination room may include the position information of the ionization chamber relative to one or more components (e.g., a detector) of the scanning device 151 and/or the position of the ionization chamber in a 3D coordinate system. In some embodiments, the position of the ionization chamber relative to a detector (e.g., a flat panel detector) of the scanning device may be fixed. For example, the ionization chamber may be fixed at a fixed position relative to the detector. The position of the ionization chamber relative to the detector may be unchanged during different scanning operations. The operator and/or the scanning device may adjust the position of the detector based on the position of the ROI of the object before the scan. The processing device 110 may obtain the position of the detector of the scanning device in the examination room and the fixed position of the ionization chamber relative to the detector of the scanning device to determine the position information of the ionization chamber in the examination room. In some embodiments, the position of the ionization chamber relative to the detector of the scanning device may be adjustable. For example, the ionization chamber may be mounted in a removable cassette. A position sensor may be mounted in the cassette and/or other components of the scanning device. The processing device 110 may obtain data detected by the position sensor to determine the position of the ionization chamber. In some embodiments, the position information of the ionization chamber in the examination room may be the position of the ionization chamber in the 3D coordinate system. For example, the 3D coordinate system may be established in the examination room for describing the position of the ionization chamber and/or other components (e.g., the detector, the projection device 152) of the system 100.

In operation 320, a detection region of at least one ionization chamber of the one or more ionization chambers may be determined based on the position information of the one or more ionization chambers.

Specifically, the operation may be performed by a detection region determination module 620.

In some embodiments, the detection region of the ionization chamber may be related to the position information of the ionization chamber. The detection region of the ionization chamber may be a fixed range around the ionization chamber, and may be, for example, a circular region, a square region, a triangular region, or other shaped region with a fixed size. The size and the shape of the detection region may be related to the size of the ionization chamber. In some embodiments, the dimension (e.g., a radius, a side length, an area, etc.) of the region may be preset in the system 100. The processing device 110 may determine an actual detection region of an ionization chamber based on the position information of the ionization chamber and the dimension of the detection region. In some embodiments, the processing device 110 may determine a detection region of one ionization chamber of the one or more ionization chambers. In some embodiments, the processing device 110 may determine a detection region of each of the multiple ionization chambers. In some embodiments, the processing device 110 may determine detection regions of a part of the ionization chambers of the one or more ionization chambers. For example, after determining the position information of the multiple ionization chambers, the processing device 110 may further determine detection regions of ionization chambers that are close to a specific position (e.g., a center point, an upper portion, a lower part, etc.) of the flat panel detector.

In operation 330, projection data of a projection device may be determined. The projection data may include image data corresponding to the detection region of the at least one ionization chamber.

Specifically, the operation may be performed by a projection data determination module 630.

In some embodiments, the processing device 110 may determine the projection data of the projection device 152. The projection data may include image data corresponding to the detection region of the at least one ionization chamber of the one or more ionization chambers (hereinafter referred to as the "at least one ionization chamber"). The image data may be data generated based on the actual detection region of the at least one ionization chamber. The image data may be color image data or grayscale image data. In some embodiments, when the processing device 110 determines the detection regions of the multiple ionization chambers, the image data may include multiple graphics (e.g., circles, squares, etc.). Each graphic may correspond to a detection region of the ionization chamber, respectively. The graphic may be a color filled graphic or lines depicting an outline of the detection region of the ionization chamber. The detection regions may be represented by the same color and/or graphic, or by different colors and/or graphics. In some embodiments, the processing device 110 may obtain a position of the projection device in the examination room, and determine a size of the graph corresponding to the detection region of the ionization chamber based on one or more of the position of the projection device, the position of the ionization chamber, the detection region of the ionization chamber, the body thickness of the object, etc., such that the detection region of the ionization chamber projected onto the object consistent with a size of the actual detection region of the ionization chamber. The projection device may be used to project the projection data onto the object to be scanned, to mark the detection region of the ionization chamber. In some embodiments, the projection data may further include other forms of data or parameters, such as a projection direction, a brightness, a resolution, a contrast level, or the like, or any combinations thereof. At least part of the data or the parameters may be default values, or values that are manually set by a user (e.g., an operator). The projection direction may be a direction from the lens of the projection device to a center point of the detector (or a center point of the detection region of the at least one ionization chamber). In some embodiments, the image data may include a graphic, a text, a pattern, an icon, a number, etc.

In operation 340, the projection device may be controlled to project the projection data onto the object.

Specifically, the operation may be performed by a control module 640.

In some embodiments, the processing device 110 may control the projection device 150 to project the projected data onto the object. The projection device 152 may be and/or include any suitable device capable of projecting image data. For example, the projection device 152 may be a cathode ray tube (CRT) projector, a liquid crystal display (LCD) projector, a digital light processor (DLP) projector, a digital light path vacuum tube (DLV) projector, or other device capable of projecting image data. In some embodiments, the projection device 152 may project the projection data onto the object using a central projection mode or a parallel projection mode. When the parallel projection mode is used, the projection device 152 may project the projection data onto the object using an orthographic projection mode or an oblique projection mode. Preferably, the projection data may be projected onto the object using the orthographic projection mode.

The projection data may include image data corresponding to the detection region of the at least one ionization chamber. For example, the projection device may project the data to be projected toward a center point of the detector. The image data corresponding to the detection region of the at least one ionization chamber may be projected onto the body surface of the object due to an occlusion of the object, thereby marking the detection region of the at least one ionization chamber. The operator may observe the projected detection region of the at least one ionization chamber easily, and determine whether the at least one ionization chamber includes one or more candidate ionization chambers. As used herein, the term "candidate ionization chamber" may refer to an ionization chamber that is covered by the ROI to be scanned of the object. In some embodiments, the operator may determine an approximate range of the ROI by visual inspection. In some embodiments, the projection data projected onto the object by the projection device may also include image data corresponding to the ROI. For example, the ROI may be represented by a color-filled graphic (e.g., a rectangle), or a colored line may be used to depict an outline of the ROI. Different display modes may be used to distinguish the ROI and the detection region of the ionization chamber. For example, different colors may be used to represent the ROI and the detection region of the ionization chamber. For example, lines may be used to depict the outline of the ROI, while color-filled graphics may be used to represent the detection region of the ionization chamber. This projection mode may facilitate the operator to visually observe whether the ROI of the object covers at least a part of the detection region of the ionization chamber in the at least one ionization chamber. Optionally, the operator may use a laser positioning light to project on the object to observe the range of the ROI. In some embodiments, the processing device 110 may determine the ROI of the object automatically. The ROI may be determined by a method commonly used by those skilled in the art, which is not limited in the present disclosure. For example, the processing device 110 may obtain an image (e.g., a reference image described in FIG. 4) including a portion to be scanned of the object (e.g., the chest, the lower extremity), and determine the ROI of the object using a template matching algorithm, a machine learning model, etc.

If the operator determines that the at least one ionization chamber does not include any candidate ionization chamber (i.e., the ROI of the object does not cover the detection region of any ionization chamber of the at least one ionization chamber), the operator may adjust positions of one or more ionization chambers (also referred to as the reference ionization chambers) of the at least one ionization chamber relative to the ROI of the object (e.g., the patient). For example, the operator may instruct the patient to change the position or the posture. As another example, if the ionization chamber can be moved relative to the detector, the operator may adjust the position of the one or more reference ionization chambers relative to the detector. As another example, the operator may adjust the position of the detector (e.g., move the detector in an up and down and/or left and right direction), thereby changing the positions of the one or more reference ionization chambers relative to the ROI of the object. After the position of the ionization chamber relative to the ROI is adjusted, the processing device 110 may repeat the process 300, to facilitate the operator to determine whether the detection region of at least one reference ionization chamber of the one or more reference ionization chambers is covered by the ROI. In some embodiments, if the positions of the one or more reference ionization chambers are changed, the processing device 110 may update the projection data in real time, such that the projection data reflects changed actual detection regions of the one or more reference ionization chambers, so that the user can observe and determine whether to continue to adjust the positions of the one or more reference ionization chambers.

In some embodiments, the processing device 110 may also adjust the positions of the one or more ionization chambers (also referred to as the reference ionization chambers) of the at least one ionization chamber relative to the ROI of the object (e.g., a patient) by controlling a movement of the scanning table 151-4 on which the target object is placed. For example, the processing device 110 may generate a movement control instruction based on the positions of the one or more reference ionization chambers relative to the detector, and control the movement of the scanning table 151-4 based on the movement control instruction, to adjust the positions of the one or more ionization chambers of the at least one ionization chamber relative to the ROI of the object. Further, the processing device 110 may obtain a virtual model of the scanning table 151-4, and control the movement of the scanning table 151-4 supporting the target object based on the virtual model of the scanning table 151-4. For example, the processing device 110 may generate the movement control instruction based on the positions of the one or more reference ionization chambers relative to the detector. The processing device 110 may control one of the virtual model and the scanning table 151-4 to perform the movement control instruction. The other one of the virtual model and the scanning table 151-4 may perform a same movement as the virtual model or the scanning table 151-4 that obtains the movement control instruction. For example, the scanning table 151-4 may obtain the movement control instruction from the processing device 110, and perform a corresponding movement automatically based on the movement control instruction. In some embodiments, when the scanning table 151-4 receives the movement control instruction to perform a current movement, the processing device 110 may obtain current movement information of the scanning table 151-4. In some embodiments, the process of performing the same movement may be implemented based on a mapping relationship between a device coordinate system of the scanning table 151-4 and a model coordinate system of the virtual model. For example, when the scanning table 151-4 performs the current movement, the processing device 110 may obtain the current movement information of the scanning table 151-4, map position information (e.g., coordinates in the device coordinate system) in the current movement information of the scanning table 151-4 to the model coordinate system, and then control the virtual model to move to a position based on mapped position information (e.g., coordinates in the model coordinate system). The virtual model may display the movement of the medical treatment device synchronously, which may be convenient for the operator to observe and monitor the movement and the parameters of the medical treatment device, further improving the interaction between medical treatment device and the user, and convenient for the operator to use.

Further, if the operator determines that the at least one ionization chamber includes one or more candidate ionization chambers (i.e., the ROI of the object covers at least a part of the detection region of the ionization chamber in the at least one ionization chamber), the user may select one or more target ionization chambers from the one or more candidate ionization chambers via a terminal (e.g., the terminal 130). The processing device 110 may obtain a user input from the terminal 130 to determine the selected target ionization chamber(s). Optionally, the processing device 110 may adjust the projection data of the projection device 152 such that the image data corresponding to the detection regions of the one or more target ionization chambers in the projection data is visually distinct from image data corresponding to detection regions of other ionization chambers. More descriptions for adjusting the projection data after determining the target ionization chamber may be found in FIG. 5.

In some embodiments, the processing device 110 may determine whether the at least one ionization chamber includes the one or more candidate ionization chambers automatically. Specifically, the processing device 110 may determine whether the ROI of the object covers at least a part of the detection region of the ionization chamber in the at least one ionization chamber automatically. In response to determining that the ROI of the object covers at least a part of the detection region of the at least one ionization chamber, the processing device 110 may designate an ionization chamber whose detection region is covered as a candidate ionization chamber. Optionally, the processing device 110 may select one or more target ionization chambers from the one or more candidate ionization chambers automatically. More descriptions of the automatic determination process may be found in FIG. 4.

Figure 4:
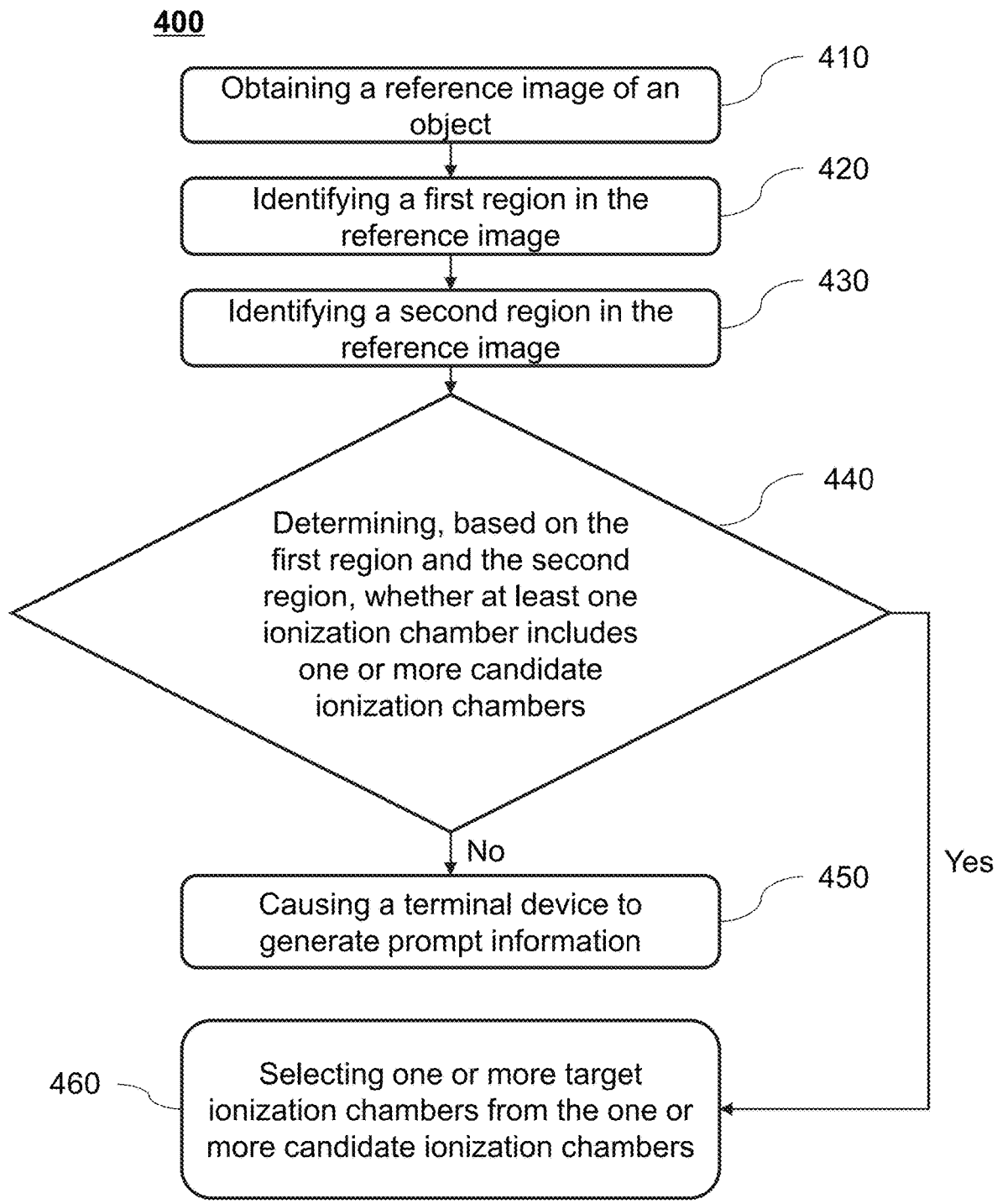
FIG. 4 is a flowchart illustrating an exemplary process for automatically selecting a target ionization chamber according to some embodiments of the present disclosure.

FIG. 4 is a flowchart illustrating an exemplary process for automatically selecting a target ionization chamber according to some embodiments of the present disclosure. Specifically, the process 400 may be executed by the processing device 110. For example, the process 400 may be stored in a storage device (e.g., the storage device 120) in a form of a program or instructions, and when the system 100 executes the program or the instructions, the process 400 for automatically selecting a target ionization chamber may be implemented. As shown in FIG. 4, the process 400 may include the following operations.

In operation 410, a reference image of the object may be obtained. The reference image may be captured by a camera after the projection device projects the projection data onto the object to be scanned.

In some embodiments, operation 410 may be performed by the obtaining module 610.

In some embodiments, an image capture device (e.g., a camera) of the system 100 may capture the reference image of the object. For example, after the projection device projects the projection data onto the object to be scanned, the processing device 110 (e.g., the control module 640) may control the camera to capture the reference image of the object. While capturing the image data of the object, the camera may also capture a graphic projected on the object. In some embodiments, the reference image may include an ROI of the object and a marked detection region of at least one ionization chamber projected on the object. In some embodiments, the graphic projected on the object by the projection device may include a graphic corresponding to the detection region of the at least one ionization chamber and a graphic corresponding to the ROI of the object. Accordingly, the reference image may include the ROI marked by the projection and the detection region of the at least one ionization chamber.

The image capture device may be and/or include any suitable device capable of capturing image data of the object. For example, the image capture device may include a camera (e.g., a digital camera, an analog camera, etc.), a camera, a red, green, and blue (RGB) sensor, an RGB depth (RGB-D) sensor, or other device capable of capturing image data of the object. Preferably, the image capture device (e.g., the camera) may capture the reference image of the object in an orthophoto way. The image capture device (e.g., a camera) may also capture the reference image of the object by other ways (e.g., an oblique photography, etc.), which is not limited in the present disclosure.

In operation 420, a first region in the reference image may be identified. The first region may correspond to the region of interest to be scanned of the object.

In some embodiments, the projection data of the projection device may not include image data corresponding to the ROI. The processing device 110 (e.g., the candidate ionization chamber determination module 650) may identify the first region corresponding to the ROI in the reference image. For example, the processing device 110 may determine the ROI of the object in the reference image using a template matching algorithm, a machine learning model, etc., which is not limited in the present disclosure. Merely by way of example, if the machine learning model is used, the reference image may be input into a trained machine learning model, and the trained machine learning model may output an identified first region after processing the reference image. Training samples for training the machine learning model may include multiple sample images and ROIs manually labeled based on the sample images.

In some embodiments, the projection data of the projection device may include the image data corresponding to the ROI. The processing device 110 may identify the first region in the reference image using an image identification algorithm. For example, the image identification algorithm may include an identification algorithm based on an image feature such as a color feature, a texture feature, a shape feature, and a local feature point. In some embodiments, a component (e.g., the terminal 130) of the system 100 may display the first region on a display interface of the terminal.

In operation 430, a second region in the reference image may be identified. The second region may correspond to the detection region of at least one ionization chamber projected onto the object.

In some embodiments, the processing device 110 may identify the second region corresponding to the detection region of the at least one ionization chamber in the reference image using an image identification algorithm. For example, the image identification algorithm may include an identification algorithm based on an image feature such as a color feature, a texture feature, a shape feature, and a local feature point. In some embodiments, the second region corresponding to the detection region of the at least one ionization chamber projected onto the object may include multiple separated regions. For example, when the projection data includes image data of detection regions of two ionization chambers, the second region may include two separated sub-regions. Each sub-region may correspond to a detection region of one ionization chamber, respectively.

In operation 440, a determination may be made as whether the at least one ionization chamber includes one or more candidate ionization chambers based on the first region and the second region.

In some embodiments, operation 440 may be performed by the candidate ionization chamber determination module 650. For example, a component (e.g., the processing device 110) of the system 100 may determine whether the first region covers the second region or at least one sub-region of one or more sub-regions of the second region. In response to determining that the first region covers the second region or the at least one sub-region of the one or more sub-regions of the second region, the processing device 110 may determine that the at least one ionization chamber includes the at least one candidate ionization chamber. The target ionization chamber may be selected from the candidate ionization chamber(s). If the first region does not cover the second region or any sub-region of the second region, the processing device 110 may determine that the at least one ionization chamber does not include any candidate ionization chamber.

It should be noted that the above judgments may be automatically performed by the component (e.g., the processing device 110) of the system 100 based on the first region and the second region, or may be manually performed by a user. For example, the user may make an artificial judgment based on the first region and the second region displayed on the display interface of the component (e.g., the terminal 130) of the system 100, and input a judgment result into the terminal 130.

In operation 450, in response to determining that the at least one ionization chamber does not include any candidate ionization chamber, a terminal device may be caused to generate prompt information.

In some embodiments, operation 450 may be performed by the candidate ionization chamber determination module 650.

For example, the prompt information may be in a form of a text, a voice, an image, a video, an alert, or the like, or any combination thereof. For example, the prompt information may be in the form of the text and the voice. When the processing device 110 determines that the ROI does not cover a detection region of any ionization chamber of the at least one ionization chamber, the display interface of the terminal 130 may display the text for prompt (e.g., "ROI does not cover the detection region of any ionization chamber detection"), and the terminal 130 may issue a voice prompt corresponding to the text at the same time. As another example, the prompt information may be in the form of the image. When a component (e.g., the processing device 110) of the system 100 determines that a detection region of any ionization chamber of the at least one ionization chamber does not cover the region of interest, a part of the display interface of the terminal 130 for displaying the first region and/or the second region may change color and/or flash to prompt the user. In some embodiments, after receiving the prompt information, the user may manually change positions of the one or more reference ionization chambers of the at least one ionization chamber relative to the ROI to be scanned, such that the ROI covers a detection region of at least one reference ionization chamber of the one or more reference ionization chambers. For example, the user may adjust the positions of one or more reference ionization chambers. As another example, the user may adjust the posture and/or the position of the object, so that the ROI of the object is moved relative to the one or more reference ionization chambers, such that the ROI covers the detection region of the at least one reference ionization chamber of the one or more reference ionization chambers.

In some embodiments, in response to determining that the at least one ionization chamber does not include any candidate ionization chamber, a component (e.g., the processing device 110) of the system 100 may cause one or more reference ionization chambers of the at least one ionization chamber to be moved relative to the ROI of the object, such that the ROI covers the detection region of the at least one reference ionization chamber of the one or more reference ionization chambers.

In operation 460, in response to determining that the at least one ionization chamber includes one or more candidate ionization chambers, one or more target ionization chambers may be selected from the one or more candidate ionization chambers. The one or more target ionization chambers may operate during a scan of the object.

In some embodiments, operation 460 may be performed by a target ionization chamber determination module 660.

In some embodiments, in response to determining that the at least one ionization chamber includes the one or more candidate ionization chambers, the processing device 110 may select one or more target ionization chambers from the one or more candidate ionization chambers. The one or more target ionization chambers may operate during the scan of the object.

In some embodiments, the processing device 110 may select the one or more target ionization chambers close to the ROI of the object from the one or more candidate ionization chambers. For example, the processing device 110 may select the one or more target ionization chambers close to the ROI from the candidate ionization chambers based on a distance between the candidate ionization chamber and the ROI. The distance between the candidate ionization chamber and the ROI may refer to a distance between a point (e.g., a center point) of the candidate ionization chamber and a point (e.g., a center point) of the ROI. The processing device 110 may determine the distance between the candidate ionization chamber and the ROI based on position information of the candidate ionization chamber and position information of the ROI. Merely by way of example, for a candidate ionization chamber, the processing device 110 may determine a distance between the candidate ionization chamber and the ROI. The processing device 110 may determine whether the distance is less than a distance threshold (e.g., 2 cm). If the distance between the candidate ionization chamber and the ROI is less than the distance threshold, the processing device 110 may determine that the candidate ionization chamber is in a vicinity of the ROI, and designate the candidate ionization chamber as a target ionization chamber. As another example, the processing device 110 may select a candidate ionization chamber that is closest to the ROI from the multiple candidate ionization chambers, i.e., the candidate ionization chamber with the smallest distance from the ROI, as the target ionization chamber. Optionally, the processing device 110 may also select the candidate ionization chamber that is closest to a significant part of the ROI as the target ionization chamber. For example, when the ROI is the chest cavity, the processing device 110 may select the candidate ionization chamber that is closest to the heart as the target ionization chamber. Optionally, the processing device 110 may also select one or more target ionization chambers from the candidate ionization chambers randomly.

FIG. 5 is a flowchart illustrating an exemplary process for adjusting projection data according to some embodiments of the present disclosure. Specifically, the process 500 may be executed by the processing device 110. For example, the process 500 may be stored in a storage device (e.g., the storage device 120) in a form of a program or instructions, and when the system 100 executes the program or the instructions, the process 500 for adjusting the projection data may be implemented. As shown in FIG. 5, the process 500 may include the following operations.

In operation 510, identification information of one or more target ionization chambers selected from the at least one ionization chamber may be obtained.

In some embodiments, operation 510 may be performed by the target ionization chamber determination module 660.

In some embodiments, the processing device 110 may obtain the identification information of the one or more target ionization chambers selected from the at least one ionization chamber. The identification information may be information used to distinguish different ionization chambers. For example, the identification information may be a number of the ionization chamber, position information of the ionization chamber, and/or other information that can distinguish the target ionization chamber from other ionization chambers. The one or more target ionization chambers may be manually determined by a user after observing a projection result (e.g., the image data projected by the projection device in operation 340 in process 300), or may be automatically determined by the processing device 110 (e.g., according to process 400).

In operation 520, the projection data may be adjusted based on the identification information, such that a first feature value of image data corresponding to detection regions of the one or more target ionization chambers in the projection data is different from a second feature value of image data corresponding to detection regions of the other ionization chambers. The first feature value and the second feature value may correspond to a same image feature.

In some embodiments, the image feature may be a feature characterizing different properties of an image, such as a filled color of the image, a color of an image outline, a thickness of the image outline, etc. The first feature value and the second feature value may be different feature values corresponding to the same image feature. By making the first feature value of the image data corresponding to the detection regions of the one or more target ionization chambers in the projection data different from the second feature value of the image data corresponding to the detection regions of the other ionization chambers, the user may easily distinguish the detection regions of the target ionization chambers from the detection regions of the other ionization chambers projected onto the object. For example, for the image feature is a color of the image, the first feature value may be red and the second feature value may be green. Before the projection data is adjusted, the color of the graphics corresponding to the detection regions of all of the ionization chambers in the at least one ionization chamber may be green. A component (e.g., the processing device 110) of the system 100 may change the color of the graphics of the detection regions of the target ionization chambers to red based on the identification information, and the color of the graphics of the detection regions of the other ionization chambers may remain unchanged in green, so as to achieve the purpose of distinguishing the target ionization chambers from the other ionization chambers. As another example, for the image feature is a width of an image border, the first feature value may be 5 mm and the second feature value may be 1 mm. In some embodiments, the image feature may also be a text and/or a symbol. For example, the image feature may be an arrow. At this time, the feature value of the image feature may be that whether it includes the arrow or not. For example, for the image feature, the first feature value may be that the arrow is included, and the second feature value may be that the arrow is not included. Similarly, the image feature may also be a text, such as "selected", etc. In some embodiments, the first feature value and/or the second feature value may be preset in the system 100, or may be set by a user in an operation (e.g., via the terminal 130). For example, the user may set the first feature value of the image feature corresponding to the color of the image to yellow via the terminal 130.

FIG. 6 is a schematic block diagram illustrating a system for marking a detection region of an ionization chamber according to some embodiments of the present disclosure. As shown in FIG. 6, the components (e.g., the processing device 110) of the system 600 for marking the detection region of the ionization chamber may include an obtaining module 610, a detection region determination module 620, a projection data determination module 630, and a control module 640. Optionally, in some embodiments, the components (e.g., the processing device 110) of the system for marking the detection region of the ionization chamber may also include a candidate ionization chamber determination module 650, and a target ionization chamber determination module 660.

The obtaining module 610 may be configured to obtain position information of one or more ionization chambers of a scanning device (e.g., the scanning device 151). In some embodiments, a position of the ionization chamber relative to the detector of the scanning device may be fixed. The obtaining module 610 may obtain the position of the detector of the scanning device in the examination room and the fixed position of the ionization chamber relative to the detector of the scanning device, to determine the position information of the ionization chamber in the examination room. In some embodiments, the position of the ionization chamber relative to the detector of the scanning device may be adjustable. For example, the ionization chamber may be mounted in a removable cassette. A position sensor may be mounted in the cassette and/or other components of the scanning device. In this case, the obtaining module 610 may obtain data detected by the position sensor to determine the position of the ionization chamber. In some embodiments, the position information of the ionization chamber in the examination room may be a position of the ionization chamber in a 3D coordinate system. For example, the 3D coordinate system may be established in the examination room for describing the position of the ionization chamber and/or other components (e.g., the detector, the projection device 152) of the system 100. More descriptions of the obtaining module 610 may be found elsewhere in the present disclosure (e.g., operation 310), which is not repeated here.

The detection region determination module 620 may be configured to determine a detection region of at least one ionization chamber of one or more ionization chambers based on position information of the one or more ionization chambers. In some embodiments, the detection region of the ionization chamber may be related to the position information of the ionization chamber. For example, a size and a shape of the detection region may be related to a size of the ionization chamber. In some embodiments, a dimension (e.g., a radius, a side length, an area, etc.) of the detection region may be preset in the system 100. The detection region determination module 620 may determine an actual detection region of the ionization chamber based on the position information of the ionization chamber and the dimension of the detection region. More descriptions of the detection region determination module 620 may be found elsewhere in the present disclosure (e.g., operation 320), which is not repeated here.

The projection data determination module 630 may be configured to determine projection data of a projection device. The projection data may include image data corresponding to a detection region of at least one ionization chamber. In some embodiments, the projection data may further include image data corresponding to an ROI of an object to be scanned. More descriptions of the projection data determination module 630 may be found elsewhere in the present disclosure (e.g., operation 330), which is not repeated here.

The control module 640 may be configured to control the projection device 152 to project the projected data onto the object to be scanned. The projection device 152 may be and/or include any suitable device capable of projecting the image data. For example, the projection device 152 may be a cathode ray tube (CRT) projector, a liquid crystal display (LCD) projector, a digital light processor (DLP) projector, a digital light path vacuum tube (DLV) projector, or other device capable of projecting image data. More descriptions of the control module 640 may be found elsewhere in the present disclosure (e.g., operation 340), which is not repeated here.

The candidate ionization chamber determination module 650 may be configured to determine whether at least one ionization chamber includes one or more candidate ionization chambers. For example, the candidate ionization chamber determination module 650 may identify a first region corresponding to an ROI from a reference image. In some embodiments, the candidate ionization chamber determination module 650 may also be configured to determine whether the at least one ionization chamber includes the one or more candidate ionization chambers based on the first region and the second region. In some embodiments, the candidate ionization chamber determination module 650 may also be configured to, in response to determining that the at least one ionization chamber does not include any candidate ionization chamber, cause a terminal (e.g., the terminal 130) to generate prompt information. More descriptions of the candidate ionization chamber determination module 650 may be found elsewhere in the present disclosure (e.g., operation 420, operation 440, operation 450, etc.), which is not repeated here.

The target ionization chamber determination module 660 may determine one or more target ionization chambers. For example, in response to determining that the at least one ionization chamber includes the one or more candidate ionization chambers, the target ionization chamber determination module 660 may select the one or more target ionization chambers from the one or more candidate ionization chambers. The one or more target ionization chambers may operate during the scan of the object. In some embodiments, the target ionization chamber determination module 660 may select the one or more target ionization chambers in a vicinity of the ROI of the object from the multiple candidate ionization chambers. More descriptions of the target ionization chamber determination module 660 may be found elsewhere in the present disclosure (e.g., operation 460), which is not repeated here.

It should be noted that the above descriptions of the system for marking the detection region of the ionization chamber and the device/module thereof are only for convenience of description, and cannot limit the present disclosure to the scope of the embodiments. It should be understood that, for those skilled in the art, after understanding the principle of the system, various devices/modules may be combined or a subsystem may be formed to connect with other devices/modules without departing from this principle. For example, the obtaining module 610, the detection region determination module 620, the projection data determination module 630, and the control module 640 disclosed in FIG. 6 may be different modules in one device (e.g., the processing device 110), or one module that can implement the functions of two or more of the above modules. For example, the detection region determination module 620 and the projection data determination module 630 may be two modules, or one module having the functions of both of the two modules. As another example, the candidate ionization chamber determination module 650 and the target ionization chamber determination module 660 may be omitted. Those variations and modifications do not depart from the scope of the present disclosure.

Some embodiments of the present disclosure may also disclose a computer-readable storage medium. The storage medium may store computer instructions. When the computer instructions are read by a computer, the computer may effectuate a method for marking a detection region of an ionization chamber provided in the present disclosure.

Some embodiments of the present disclosure may also disclose a device for marking a detection region of an ionization chamber. The device may include a program for marking the detection region of the ionization chamber. The program may effectuate the method for marking the detection region of the ionization chamber provided in the present disclosure.

The possible beneficial effects of the embodiments of the present disclosure may include but are not limited to the followings. (1) By projecting the projection data to be projected (e.g., the image data of the detection region of the ionization chamber) onto the object by the projection device, the detection region of the ionization chamber can be clearly and effectively marked or represented, and the obstacle of lack of the marking of the detection region of the ionization chamber or the marking of the detection region obscured by the object can be overcome. (2) By obtaining the reference image of the object and identifying the reference image, it can automatically determine whether the region of interest to be scanned of the object covers the detection region of the at least one ionization chamber of the one or more ionization chambers. By generating the prompt information and/or controlling the movement of the ionization chamber, the accuracy of the object to be scanned or the region of interest covering the detection region of the ionization chamber can be improved, and the time and effort required by the operator can also be reduced. It should be noted that different embodiments may produce different beneficial effects, and in different embodiments, the possible beneficial effects may be any one or any combination of the above, or any other beneficial effects that may be obtained.

The working environment of the medical treatment device (e.g., an X-ray camera, an angiography machine, etc.) may often be isolated from the operator. When using the medical treatment device for a medical diagnosis and treatment operation (e.g., an image acquisition), the operator may often only rely on a control instruction to control a diagnosis and treatment action. Usually, during the medical diagnosis and treatment, the operator cannot observe a specific movement of the medical treatment device in real time, and cannot know a movement parameter of a moved component of the medical treatment device. Therefore, it is necessary to provide a method for controlling the medical treatment device, to enhance the interaction between the operator and the medical treatment device.

FIG. 7 is a flowchart illustrating an exemplary process for controlling a medical treatment device according to some embodiments of the present disclosure. In some embodiments, process 700 may include following operations.

In operation 710, a virtual model of a medical treatment device may be obtained. In some embodiments, operation 710 may be performed by a model obtaining module 1110.

The medical treatment device may be an automated device that performs a medical diagnosis and treatment task. In some embodiments, the medical diagnosis and treatment task may include, but are not limited to, a medical camera task, a surgical task, a rehabilitation treatment task, or the like. In some embodiments, the medical treatment device may include an X-ray camera system, a digital subtraction angiography (DSA) device, or the like. In some embodiments, the medical treatment device may include at least one movable first component. In some embodiments, when the medical treatment device is an X-ray camera system, the first component may include an X-ray camera gantry, i.e., a gantry of the X-ray camera system. In some embodiments, the X-ray camera gantry may include multiple components. The multiple components may include, but are not limited to, one or more of a tube, a detector, a support element of the tube, and a support element of the detector.

The virtual model may be a virtual shape structure of the medical treatment device (e.g., the X-ray camera system) constructed by the processing device. In some embodiments, the virtual model may have a same or similar appearance as a solid structure of the medical treatment device. In some embodiments, the virtual model may be visualized by a display device. In some embodiments, the virtual model may be three-dimensional or two-dimensional. In some embodiments, the virtual model may include a second component corresponding to the first component of the medical treatment device. In some embodiments, a device coordinate system in which the first component is located may have a mapping relationship with a model coordinate system in which the second component is located. The device coordinate system may refer to a coordinate system constructed based on an actual environment in which the medical treatment device is located. The model coordinate system may refer to a coordinate system constructed in the virtual model. In some embodiments, the mapping relationship may be a corresponding relationship between coordinates of a point on the first component in the device coordinate system and coordinates of a corresponding point on the second component in the model coordinate system. In some embodiments, the corresponding relationship may be that coordinate values are the same. For example, coordinates of a point A on the first component in the device coordinate system may be (10, 10, 10). Correspondingly, coordinates of a corresponding point A' on the second component in the model coordinate system may be (10, 10, 10). The point A and the point A' may have a corresponding relationship.

In some embodiments, the virtual model may be obtained by modeling data of the medical treatment device. In some embodiments, the data for modeling may be geometric data (e.g., geometric coordinates of each endpoint, a length of each side line, etc.) of the solid structure of the medical treatment device. For example, the processing device may construct the virtual model of the medical treatment device in a virtual modeling environment by scaling the geometric data of the solid structure of the medical treatment device according to a certain ratio.

In some embodiments, the virtual model may be obtained based on an image of a solid structure of the medical treatment device. For example, in some embodiments, the processing device may obtain an image or image data of the medical treatment device captured by a shooting device. In some embodiments, the processing device may extract feature points of the image or the image data according to a preset algorithm. The feature points may be points that can express a spatial distribution and a surface feature of the medical treatment device. In some embodiments, the preset algorithm may include, but is not limited to, a Harris algorithm, a Sift algorithm, a SURF algorithm, etc. In some embodiments, the processing device may extract a large number of feature points and form a point cloud. In some embodiments, the processing device may reconstruct the point cloud to obtain the virtual model of the medical treatment device. In some embodiments, the reconstruction process may be implemented according to an iterative closest point (ICP) algorithm.

In some embodiments, the virtual model may be visualized via the display interface. In some embodiments, the display interface may be a visualization interface on a display device. The display device may include, but is not limited to, a computer, a mobile terminal, a public display, a projection screen, etc.

In operation 720, current movement information of one of the first component of the medical treatment device and the second component of the virtual model may be obtained. In some embodiments, operation 720 may be performed by a movement information obtaining module 1120.

The current movement information may refer to information generated when the first component and/or the second component performs the current movement. In some embodiments, the current movement information may include movement information of one or more parts of the first component and/or the second component. In some embodiments, the current movement information may include, but is not limited to, position information, time information, or speed information, such as, but not limited to, one or more of a starting position, a target position, a movement time, and a movement speed.

In some embodiments, the first component of the medical treatment device may receive movement control information for performing the current movement. The first component may perform the current movement based on the movement control information. In some embodiments, the movement control information may include a control instruction of an automatic movement of the first component or a manual operation of the first component. For example, the first component may obtain the control instruction of the automatic movement from a medical task, and perform the corresponding medical task based on the control instruction automatically. As another example, an operator of the medical treatment device may manually operate the first component for movement. In some embodiments, when the first component performs the current movement, the processing device may obtain the current movement information of the first component.

In some embodiments, the second component of the virtual model may receive movement control information for performing the current movement. The second component may perform the current movement based on the movement control information. In some embodiments, the movement control information may be input by a mouse, a keyboard, a voice, a gesture, or by a touch. For example, the system may include a touch screen, and the operator may click or drag on the touch screen for input. As another example, the system may include a microphone, and the operator may perform a voice input using the microphone. As another example, the system may include a camera, and the camera may obtain a hand gesture of the operator as an input. As another example, the system may include an external mouse, and the operator may input via the mouse. As another example, the system may include an external keyboard, and the operator may input a text via the keyboard. For example, the operator may drag a part of the second component via the touch screen to generate the movement control information. The second component may perform the current movement based on the movement control information. In some embodiments, when the second component performs the current movement, the processing device may obtain the current movement information of the second component.

In some embodiments, real-time position information of the second component during the current movement may also be displayed on the display interface and updated with the movement. For example, height information of a part of the second component may be displayed on the display interface. More descriptions of display contents of the display interface may be found in FIG. 8B and descriptions thereof, which is not repeated here.

In operation 730, the other one of the first component of the medical treatment device and the second component of the virtual model may be controlled to perform a same movement as the one of the first component of the medical treatment device and the second component of the virtual model that obtains a movement instruction. In some embodiments, operation 730 may be performed by a movement execution module 1130.

The movement instruction may be movement control information received by the first component of the medical treatment device or the second component of the virtual model for performing the current movement.

In some embodiments, when the first component of the medical treatment device receives the movement instruction to perform the current movement, the second component of the virtual model may perform the same movement. In some embodiments, when the second component of the virtual model receives the movement instruction to perform the current movement, the first component of the medical treatment device may also perform the same movement. In some embodiments, the process of performing the same movement may be achieved based on the mapping relationship between the device coordinate system in which the first component is located and the model coordinate system in which the second component is located. For example, when the first component performs the current movement, the processing device may obtain the current movement information of the first component, map position information (e.g., coordinates in the device coordinate system) in the current movement information of the first component to the model coordinate system, and then control the movement of the second component to a position based on mapped position information (e.g., coordinates in the model coordinate system).

In some embodiments, the same movement may be a synchronous movement. In some embodiments, the processing device may obtain position information and/or speed information, for example, a starting position, a target position, and/or speed information, from the current movement information of the component that performs the current movement, and control the other component to perform the movement based on the information, so as to achieve the synchronous movement. In some embodiments, the processing device may sample the current movement information from the component that performs the current movement at a preset time interval, obtain a sampled position of the component that performs the current movement, and control the movement of the other component to a corresponding position based on the sampled position. When the preset time interval is sufficiently small or less than a threshold (e.g., 0.1 second, 0.01 second, or 0.001 second, etc.), the synchronization of the movements of the two components may be relatively good.

In some embodiments, the same movement may not be a synchronous movement. There may be a time interval between the current movement of the component and the same movement of the other component. For example, the time interval may be 5 seconds or longer. In some embodiments, the processing device may realize the same movement based on a real-time position of the two components. In some embodiments, the processing device may generate the same movement based only on the starting position and the target position of the component that performs the current movement. In some embodiments, the processing device may also generate the same movement based on the starting position, the target position, and the movement time of the component that performs the current movement. In some embodiments, the processing device may also generate the same movement based on the starting position, the target position, and the movement speed of the component that performs the current movement.

In some embodiments, when a component of the first component performs the current movement, the display interface may highlight a movement trajectory of a component of the second component corresponding to the component of the first component. The movement trajectory may be a trajectory generated when the component of the second part performs the same movement as the component of the first component.

Figure 8A:
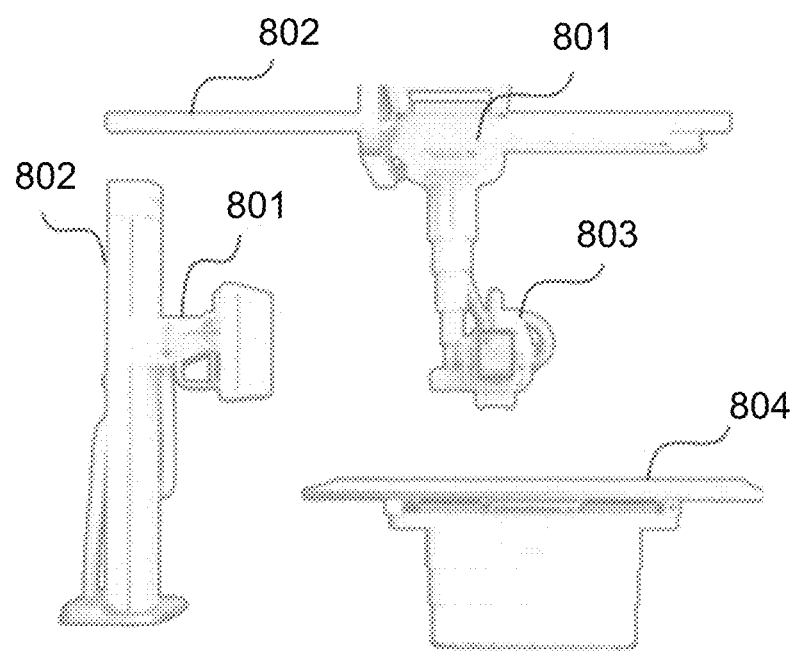
FIG. 8A is a schematic diagram illustrating an exemplary structure of a medical treatment device according to some embodiments of the present disclosure.
Figure 8B:
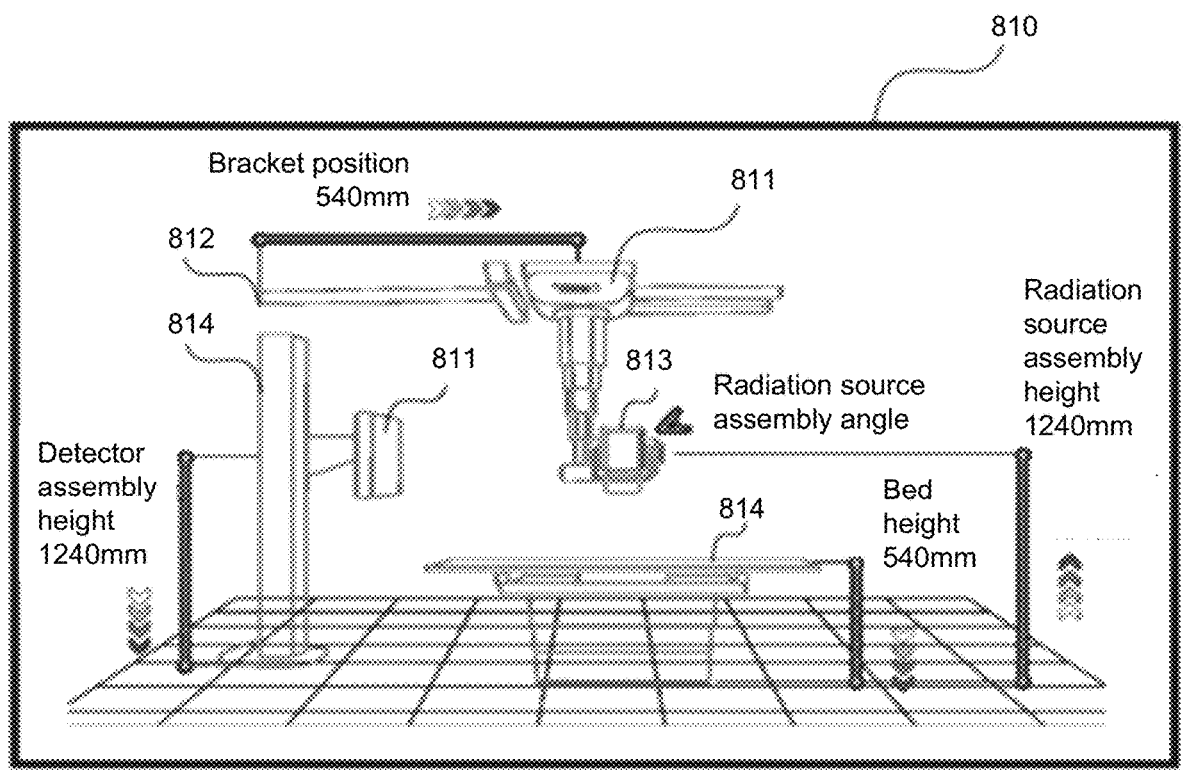
FIG. 8B is a schematic diagram illustrating an exemplary structure of a virtual model according to some embodiments of the present disclosure.

FIG. 8A is a schematic diagram illustrating an exemplary structure of a medical treatment device according to some embodiments of the present disclosure. FIG. 8B is a schematic diagram illustrating an exemplary structure of a virtual model according to some embodiments of the present disclosure.

As shown in FIG. 8A, the medical treatment device may be an X-ray camera gantry. The X-ray camera gantry may include a detector assembly 801, a rail 802, a radiation source assembly 803, and a bed 804. The detector assembly 801 and the radiation source assembly 803 may form a camera module. Typically, the radiation source assembly 803 may include a high voltage generator, a tube, and a beam limiting element. The detector unit 801 may move on the vertical rail 802. The radiation source module 803 may slide on the suspended and horizontal rail 802 via a bracket 801, and may move or rotate in a vertical direction relative to the bracket 801. The bed 804 may be raised and lowered relative to the ground.

As shown in FIG. 8B, a display interface 810 may display a virtual model of an X-ray camera gantry. The virtual model of the X-ray camera gantry may have a structure similar to the X-ray camera gantry. The virtual model of the X-ray camera gantry may include a detector assembly model 811, a rail model 812, a radiation source assembly model 813, and a bed model 814. Positions of the detector assembly model 811, the rail model 812, the radiation source assembly model 813, and the bed model 814 in the virtual model may correspond to positions of the detector assembly 801, the rail 802, the radiation source assembly 803, and the bed 804 in the X-ray camera gantry, respectively. In some embodiments, when any component of the X-ray camera gantry moves, the virtual model of the X-ray camera gantry may also perform the same movement.

In some embodiments, the display interface 810 may also display a parameter of each component of the virtual model of the X-ray camera gantry. The parameter may reflect current movement information of the each component of the X-ray camera gantry. For example, the display interface 810 may display that a horizontal position of the bracket of the radiation source assembly is 540 mm. The parameter may indicate that a current horizontal position of the bracket 801 of the radiation source assembly of the X-ray camera gantry is 540 mm. As another example, the display interface 810 may display that a direction indication for indicating a movement direction of each component of the virtual model. The movement direction may be a current movement direction of each component of the X-ray camera gantry.

FIG. 9 is a flowchart illustrating an exemplary process for controlling a medical treatment device according to some embodiments of the present disclosure. In some embodiments, process 900 may include following operations.

In operation 910, a model of an X-ray camera gantry may be obtained based on a solid structure of the X-ray camera gantry. A corresponding model movement trajectory may be simulated by using the model of the X-ray camera gantry based on a movement trajectory of the solid structure of the X-ray camera gantry.

In some embodiments, operation 910 may be performed by a movement simulation module 1210.

The X-ray camera gantry may refer to an external shape structure of an X-ray camera device. In some embodiments, the X-ray camera gantry may include multiple components. The multiple components may include, but are not limited to, one or more of a base, a bracket, a bed, a rail, a manipulator, a robotic arm, a display module, a tube, a detector, a support element of the tube, and a support element of the detector of the X-ray camera device. In some embodiments, the multiple components may include one or more driving devices for driving one or more of the multiple components to move.

The solid structure of the X-ray camera gantry may refer to a real external shape structure of the X-ray camera gantry. The model of the X-ray camera gantry (i.e., the virtual model) may refer to a virtual external shape structure of the X-ray camera gantry constructed by the processing device. In some embodiments, the model of the X-ray camera gantry may have a same or similar appearance with the solid structure of the X-ray camera gantry. In some embodiments, the model of the X-ray camera gantry may be visualized by a display device. In some embodiments, the model of the X-ray camera gantry may be three-dimensional or two-dimensional. In some embodiments, the model of the X-ray camera gantry may include one or more model components corresponding to one or more components of the solid structure of the X-ray camera gantry. In some embodiments, the one or more model components may move in the model of the X-ray camera gantry relative to other components of the model.

In some embodiments, the obtaining of the model of the X-ray camera gantry may be similar to the obtaining of the virtual model as described in FIG. 7 of the present disclosure, which is not repeated here.

In some embodiments, after the processing device obtains the model of the X-ray camera gantry, the model of the X-ray camera gantry may be used to simulate a movement trajectory of the solid structure of the X-ray camera gantry. The movement trajectory of the solid structure of the X-ray camera gantry may refer to a trajectory generated when any component of the X-ray camera gantry moves from a current position to a target position. The simulation may refer to a process of reproducing the movement trajectory of the solid structure of the X-ray camera gantry in a virtual environment using the model of the X-ray camera gantry. In some embodiments, the processing device may establish a correspondence relationship between a real coordinate of the solid structure of the X-ray camera gantry and a virtual coordinate of the model of the X-ray camera gantry, and implement the simulation based on the correspondence relationship. In some embodiments, the specific method of the simulation may be found in operation 920, operation 930, and descriptions thereof.

In operation 920, a movement instruction of a solid structure of a current X-ray camera gantry may be obtained. The movement instruction may include a target position that a component of the current X-ray camera gantry needs to move to and related movement time information.

In some embodiments, operation 920 may be performed by an instruction obtaining module 1220.

The current X-ray camera gantry may refer to an X-ray camera gantry that is currently performing a camera operation. In some embodiments, the movement instruction may be an instruction to control the current X-ray camera gantry to perform the camera operation. In some embodiments, the movement instruction may be determined based on a medical task of the current X-ray camera gantry. For example, if the current medical task is to photograph the lumbar spine, the movement instruction may include moving a camera module of the X-ray camera gantry close to the lumbar spine of a patient. In some embodiments, the movement instruction may include a target position that at least one component of the current X-ray camera gantry needs to be moved to. For example, the movement instruction may control the camera module to move to a photographing region. As another example, the movement instruction may control the camera module (e.g., a geometric center of a tube) to move to a specific coordinate point (405, 100, 405).

In some embodiments, the related movement time information may be a movement time required for a component of the current X-ray camera gantry to reach the target position determined based on historical data. The processing device may obtain the historical data of the current X-ray camera gantry. The historical data may include, when the current X-ray camera gantry receives a historical movement instruction, a historical movement time of a component of the current X-ray camera gantry to reach the target position, e.g., 2 seconds, 0.5 seconds, etc. The time may be related to the position of the current X-ray camera gantry and the historical movement instruction. For example, the historical movement instruction may include a movement speed of the current X-ray camera gantry. The historical movement time may be determined based on the position at which the current X-ray camera gantry is located, the target position, and the movement speed. In some embodiments, the processing device may determine the movement time required for the component of the current X-ray camera gantry to reach the target position based on the historical movement time. In some embodiments, the component may include, but is not limited to, a base, a manipulator, a robotic arm, and a camera module. In some embodiments, the processing device may also determine the current movement time required for multiple components of the X-ray camera gantry to reach the target position based on the historical movement time. For example, the processing device may determine an average of multiple historical movement times to determine the movement time. By determining the movement time to simulate the movement trajectory of the X-ray camera gantry, the model of the X-ray camera gantry and the movement trajectory of the solid structure of the X-ray camera gantry can be synchronized better, so the simulation can be smoother. It should be understood that, in some embodiments, the related movement time information may include multiple real-time time points related to multiple positions in a path of the component of the current X-ray camera gantry to the target position.

In operation 930, the solid structure of the X-ray camera gantry may be caused to reach the target position based on the movement instruction. A movement trajectory of the model may be simulated based on the movement instruction and the movement time information synchronously by the model of the X-ray camera gantry.

In some embodiments, operation 930 may be performed by a simulation control module 1230.

In some embodiments, the processing device may input the movement instruction into a driving device for one or more components of the X-ray camera gantry. The driving device may drive the one or more components of the X-ray camera gantry to one or more target positions based on the movement instruction. During this process, the processing device may input the movement instruction into the model of the X-ray camera gantry synchronously. In some embodiments, the processing device may map the target location in the movement instruction to the model of the camera gantry, to determine a specific position of the target position in the model. For example, the processing device may determine the specific position of the target position in the model of the X-ray camera gantry based on a correspondence relationship between real coordinates of the target position and virtual coordinates of the target position in the model of the X-ray camera gantry. In some embodiments, the processing device may control one or more components of the model of the X-ray camera gantry to move to specific positions, and a trajectory formed by this process may be the movement trajectory of the model. In some embodiments, the processing device may set a determined movement time of the solid structure of the X-ray camera gantry as a time for the model of the X-ray camera gantry to complete the movement trajectory of the model, so that the movement trajectory of the solid structure of the X-ray camera gantry and the movement trajectory of the model of the X-ray camera gantry can be completed simultaneously, to improve the real-time accuracy of the simulation. As described above, it may also be achieved by tracking time points between the gantry and the model in real time at multiple pathway positions.

In some embodiments, the simulation may also be achieved by providing an optical monitoring device in a machine room of the X-ray camera gantry for monitoring a movement of the X-ray camera gantry. For example, a position change relationship between a monitoring point on the X-ray camera gantry and a reference point may be monitored. The monitoring point may be an end point on one or more components of the X-ray camera gantry. A component may include at least one monitoring point. The reference point may be a fixed point on the X-ray camera gantry or in the machine room. The processing device may map the movement of the X-ray camera gantry monitored by the optical monitoring device to an animation of the model of the X-ray camera gantry, and realize the simulation of the movement trajectory of the X-ray camera gantry. For example, the mapping may be performed based on the position change relationship between the monitoring point and the reference point. In this embodiment, it is necessary to map the movement of the X-ray camera gantry monitored by the monitoring device to the animation of the model before realizing the effect of controlling the model to simulate the movement trajectory.

In operation 940, a simulation of the movement trajectory of the model may be displayed on a display device.

In some embodiments, operation 940 may be performed by a display module 1240.

In some embodiments, the display device may include, but is not limited to, a computer display, a cell phone display, a projection display, a public display, etc. In some embodiments, the display device may be located inside the machine room of the X-ray camera gantry, or outside the machine room of the X-ray camera gantry. In some embodiments, the display device may be a local display device or a remote display device. For example, the processing device may send the movement trajectory of the model via a network to the remote display device for display.

In some embodiments, the display device may also display a parameter change of each component of the model. In some embodiments, the parameter may include, but is not limited to, a height, a lateral movement distance, a vertical movement distance, a position coordinate, a device model, or the like. For example, the display device may synchronously display a spatial coordinate change of a component of the model when displaying a movement trajectory of the component of the model.

In some embodiments, the display device may include multiple display regions. In some embodiments, the display device may highlight a part of the model in at least one display region of the multiple display regions. In some embodiments, when a component of the solid structure of the X-ray camera gantry moves, the display device may highlight a movement trajectory of a part of the model of the X-ray camera gantry corresponding to the component on a display region. For example, the display device may include a main display region for displaying the whole model, and multiple display regions for highlighting a part of the model. In some embodiments, the display device may display a selectable view angles in a display region of the multiple display regions. The operator may cause the display device to display the movement trajectory of the model from different view angles by selecting the selectable view angles.

In some embodiments, the display device may also receive interaction data from the operator. The interaction data may be an instruction input by the operator to realize the information exchange between the operator and the solid structure of the X-ray camera gantry and its model. For example, the operator may input the instruction in the display device for controlling a display of the model of the X-ray camera gantry. In some embodiments, the display device may include a touch screen on which the operator may operate and input the interaction data. For example, the operator may input the interaction data by clicking a corresponding list or option on the touch screen. As another example, the operator may zoom in or zoom out the display of the model of the X-ray camera gantry on the touch screen. As another example, the operator may drag a part of the model of the X-ray camera gantry on the touch screen to input the interaction data. In some embodiments, the processing device may generate a movement instruction based on the interaction data input by the user on the display device, and the movement of the solid structure of the X-ray camera gantry may be controlled based on the movement instruction. For example, the display device may display an optional medical task list in one display region of the multiple display regions. The operator may generate a corresponding movement instruction for the X-ray camera gantry by clicking a medical task in the medical task list, thereby controlling the movement of the X-ray camera gantry. More descriptions of the movement of the solid structure of the X-ray camera gantry based on the interaction data input by the user on the display device may be found in FIG. 10 and descriptions thereof.

Figure 10:
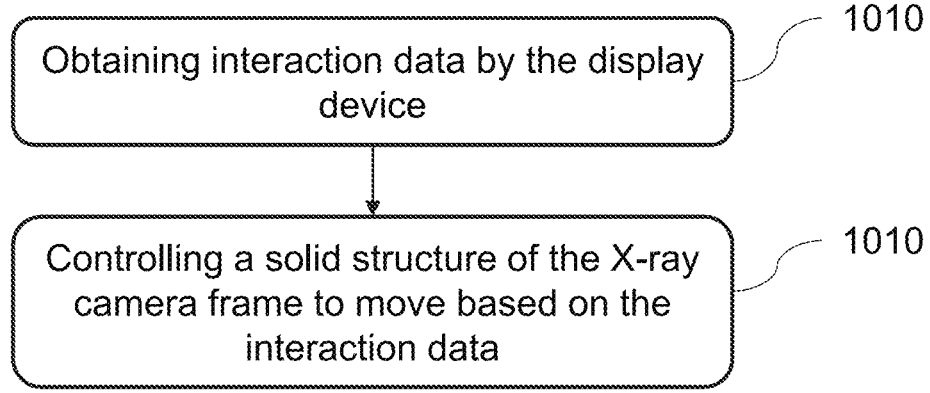
FIG. 10 is a flowchart illustrating an exemplary process for controlling a medical treatment device according to some embodiments of the present disclosure.

FIG. 10 is a flowchart illustrating an exemplary process for controlling a medical treatment device according to some embodiments of the present disclosure. In some embodiments, process 1000 may include following operations.

In operation 1010, interaction data may be obtained by the display device.

The interaction data may be input by the operator and may be used to realize the information exchange between the operator and the solid structure of the X-ray camera gantry and its model. In some embodiments, the operator may input the interaction data in the display device in various ways. The various ways may include, but not limited to, a touch input, a voice input, an image identification input, and an external device input. For example, the display device may include a touch screen, the operator may click or drag on the touch screen to input. As another example, the display device may include a microphone, and the operator may perform the voice input by using the microphone. As another example, the display device may include a camera, and the camera may obtain a hand gesture of the operator as the input. As another example, the display device may include an external mouse, and the operator may perform the input via the mouse. As another example, the display device may include an external keyboard, and the operator may perform a text input via the keyboard.

In operation 1020, a movement of the solid structure of the current X-ray camera gantry may be controlled based on the interaction data.

In some embodiments, the interaction data may include an instruction to change a display state of the model of the X-ray camera gantry. For example, the operator may switch a display angle of the model of the X-ray camera gantry based on the interaction data. As another example, the operator may zoom in or zoom out the display of the model based on the interaction data.

In some embodiments, the interaction data may include an instruction to change a movement state of the model of the X-ray camera gantry. For example, the operator may generate the interaction data by causing the model to pause the movement or start the movement. As another example, the operator may generate the interaction data by dragging a part of the model to move. In some embodiments, the processing device may generate a corresponding movement instruction based on the type of interaction data (the instruction to change the movement state of the model of the X-ray camera gantry). The generated movement instruction may be used to control the solid structure of the X-ray camera gantry to perform a movement corresponding to the model of the X-ray camera gantry. For example, when the operator pauses the movement of the model of the X-ray camera gantry on the display device, correspondingly, the movement of the solid structure of the X-ray camera gantry may also be suspended. In some embodiments, when the operator drags a part of the model of the X-ray camera gantry in the display device to move, the processing device may generate a corresponding movement instruction. A part of the solid structure of the X-ray camera gantry corresponding to the part of the model of the X-ray camera gantry may also move with the dragging trajectory based on the movement instruction. In some embodiments, the movement instruction may be generated based on the following operations: the processing device may obtain coordinates of multiple sample points on the dragging trajectory of the model, determine multiple target positions of the solid structure of the X-ray camera gantry and an order of the multiple target positions based on the coordinates of the sample points, and generate the movement instruction.

Figure 11:
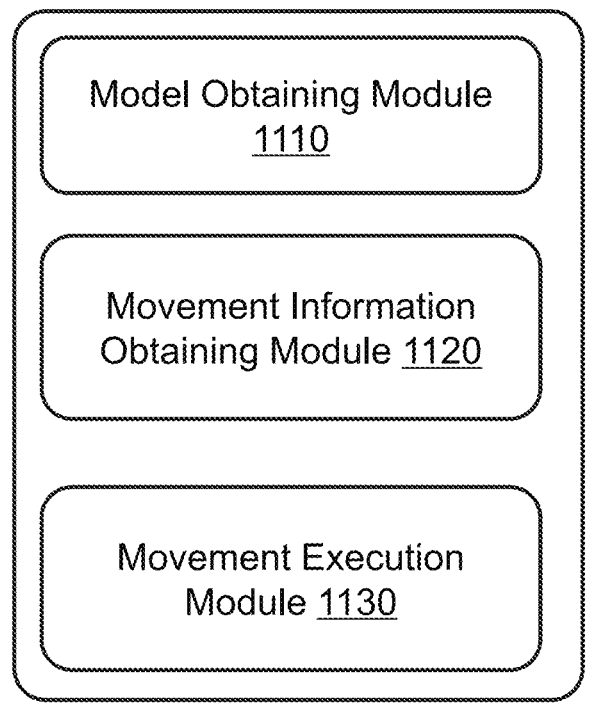
FIG. 11 is a schematic block diagram illustrating a medical treatment device control system according to some embodiments of the present disclosure.

FIG. 11 is a schematic block diagram illustrating a medical treatment device control system according to some embodiments of the present disclosure.

As shown in FIG. 11, the medical treatment device control system 1100 may include a model obtaining module 1110, a movement information obtaining module 1120, and a movement execution module 1130.

In some embodiments, the model obtaining module 1110 may be configured to obtain a virtual model of a medical treatment device. The medical treatment device may include at least one movable first component. Accordingly, the virtual model may include a second component that simulates the first component. A device coordinate system in which the first component is located may have a mapping relationship with a model coordinate system in which the second component is located.

In some embodiments, the movement information obtaining module 1120 may be configured to obtain current movement information of one of the first component of the medical treatment device and the second component of the virtual model. In some embodiments, the movement information obtaining module 1120 may also be configured to obtain the current movement information of the first component of the medical treatment device. Prior to obtaining the current movement information of the first component of the medical treatment device, the first component may obtain movement control information to perform a current movement. In some embodiments, the movement information obtaining module 1120 may also be configured to obtain the current movement information of the second component of the virtual model. Prior to obtaining the current movement information of the second component of the virtual model, the second component may obtain movement control information to perform a current movement.

In some embodiments, the movement execution module 1130 may be configured to control the other one of the first component of the medical treatment device and the second component of the virtual model to perform a same movement as the one of the first component of the medical treatment device and the second component of the virtual model that obtains a movement instruction.

Figure 12:
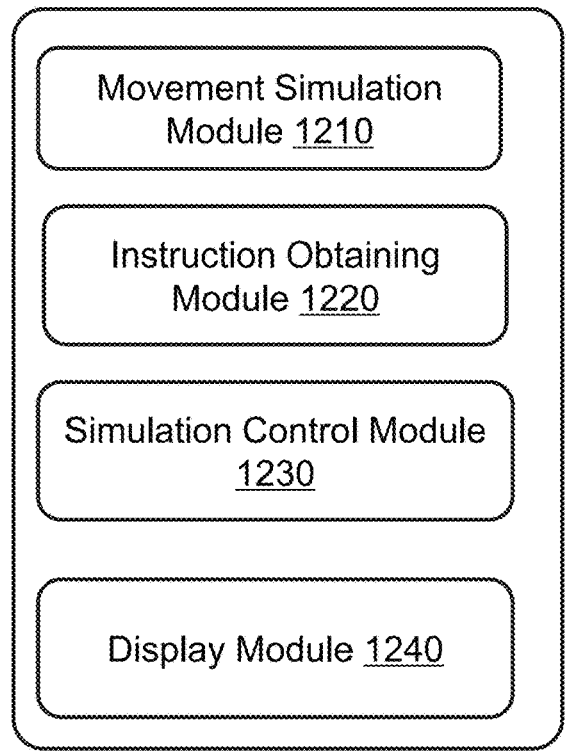
FIG. 12 is a schematic block diagram illustrating another medical treatment device control system according to some embodiments of the present disclosure.

FIG. 12 is a schematic block diagram illustrating another medical treatment device control system according to some embodiments of the present disclosure.

As shown in FIG. 12, a medical treatment device control system 1200 may include a movement simulation module 1210, an instruction obtaining module 1220, a simulation control module 1230, and a display module 1240.

In some embodiments, the movement simulation module 1210 may be configured to obtain a model of an X-ray camera gantry based on a solid structure of the X-ray camera gantry, and perform a simulation of a corresponding movement trajectory of the model using the model of the X-ray camera gantry based on the movement trajectory of the solid structure of the X-ray camera gantry.

In some embodiments, the instruction obtaining module 1220 may be configured to obtain a movement instruction of a solid structure of a current X-ray camera gantry. The movement instruction may include a target position that a component of the current X-ray camera gantry needs to move to, and a movement time required for the component of the current X-ray camera gantry to reach the target position determined based on historical data.

In some embodiments, the simulation control module 1230 may be configured to control the solid structure of the X-ray camera gantry to reach the target position based on the movement instruction. The model of the X-ray camera gantry may perform a simulation of the movement trajectory of the model based on the movement instruction within the movement time.

In some embodiments, the display module 1240 may be configured to display the simulation of the movement trajectory of the model on a display device. In some embodiments, the display module 1240 may also be configured to highlight the movement trajectory of a component of the model of the X-ray camera gantry corresponding to a component of the X-ray camera gantry on the display device.

In some embodiments, the system 1200 may further include a data obtaining module configured to obtain interaction data via the display device. In some embodiments, the obtaining module may also be configured to control the model of the X-ray camera gantry by touching on the touch screen to generate the interaction data.

In some embodiments, the system 1200 may further include a movement control module for controlling the movement of the solid structure of the current X-ray camera gantry based on the interaction data.

Some embodiments of the present disclosure may provide a device for controlling a medical treatment device, including a processor. The processor may be configured to perform computer instructions to implement the method for controlling the medical treatment device in any one or more of the above embodiments of the present disclosure.

The possible beneficial effects of the embodiments of the present disclosure may include but are not limited to the followings. (1) The movement of the medical treatment device may be displayed synchronously via the display device, which may be convenient for the operator to observe and monitor the movement and the parameter of the medical treatment device. (2) The treatment process of the medical treatment device may be displayed synchronously, which may facilitate the operator to prepare or perform a subsequent operation. (3) By determining the movement time to simulate the movement trajectory of the X-ray camera gantry, the model of the X-ray camera gantry may be synchronized with the movement trajectory of the solid structure of the X-ray camera gantry, and the simulation may be smoother. (4) By controlling the movement of the model in the display device to control the movement of the medical treatment device, the interactivity between the medical treatment device and the user may further be improved, which may be convenient for the operator to use. It should be noted that different embodiments may produce different beneficial effects, and in different embodiments, the possible beneficial effects may be any one or any combination of the above, or any other possible beneficial effects obtained.

With the development of science and technology level, he human need for medical treatment is increasing. At the same time, the requirements for obtaining the best scanning effect for the first time are also increasing. At present, a medical device is generally unable to know the patient's condition before scanning. The scanning parameter of the medical imaging device may mainly depend on the experience of a doctor or through an additional pre-scan. When setting the scanning parameter by relying on the doctor's experience, the scanning parameter may not be adjusted accurately and need to be adjusted many times. In this way, the patient may receive too much radiation dose, which may affect the patient's body. The scanning parameter may be obtained through the additional pre-scan, so that the scanning parameter may be determined after one or more pre-scans are performed on the patient. At the same time, the patient may also receive the radiation dose during the pre-scan process, which may also cause the patient to receive too much radiation dose. This may make the doctor unable to know the patient's situation in time, unable to diagnose the patient in time, and the diagnosis efficiency may be low. The patient may receive too much dose, which may affect the patient's health. Therefore, some embodiments of the present disclosure may provide a method for determining a parameter of a medical imaging device.

Figure 13:
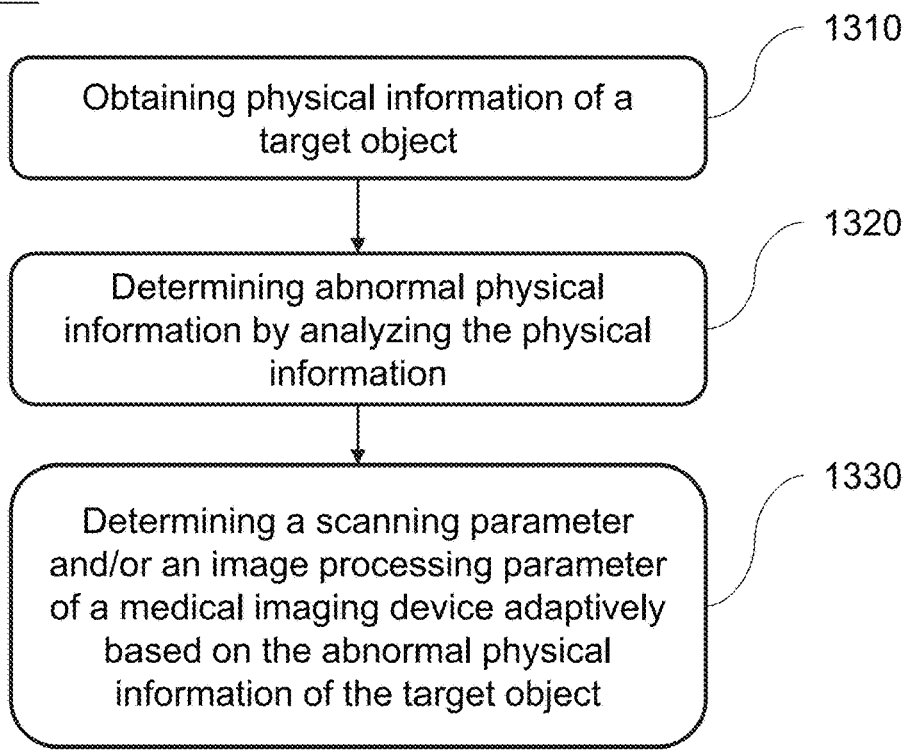
FIG. 13 is a flowchart illustrating an exemplary process for determining a parameter of a medical imaging device according to some embodiments of the present disclosure.

FIG. 13 is a flowchart illustrating an exemplary process for determining a parameter of a medical imaging device according to some embodiments of the present disclosure. This embodiment may be used to determine a scanning parameter and an image processing parameter of the medical imaging device based on physical information of a target object. The process 1300 may be performed by a device for determining a parameter of a medical imaging device. The device for determining a parameter of a medical imaging device may be implemented by software and/or hardware. The device for determining a parameter of a medical imaging device may be configured on a computing device, specifically including the following operations.

In operation 1310, physical information of a target object may be obtained.

For example, the target object may be an object to be scanned, for example, a person or an animal, etc.

The physical information may be basic physical information of the target object, such as, but not limited to, body temperature information, blood pressure information, blood lipid information, respiration information, pulse information, eye physical information, hand physical information, leg physical information, or head physical information, etc., of the target object.

It should be noted that the physical information of the target object may be obtained based on performances of the target object using a specialized instrument. Optionally, the physical information of the target object may be obtained by a sensor. For example, the sensor may be a camera, a temperature sensor, a heartbeat sensor, a respiration sensor, etc. For example, if a patient has fever symptoms, the physician may obtain body temperature information of the patient using the temperature sensor based on the fever symptoms of the patient. In this way, the physical information of the target object may be automatically obtained based on a corresponding sensor. In this way, the physical information of the target object may be automatically obtained, so that the scanning parameter and/or the image processing parameter of the medical imaging device can be determined based on the physical information.

In operation 1320, abnormal physical information may be obtained by analyzing the physical information.

For example, the abnormal physical information may be physical information that is inconsistent with standard physical information, or physical information that is inconsistent with normal physical information of the target object, etc.

Optionally, the determining the abnormal physical information by analyzing the physical information may specifically include: inputting the physical information into a trained physical identification model to obtain abnormal physical information output by the physical identification model; or comparing the physical information with a normal physical parameter to determine the abnormal physical information.

For example, the physical identification model may be a model that analyzes the input physical information and outputs the abnormal physical information. For example, the physical identification model may be a support vector machine, a fully convolutional network (FCN), a U-net neural network, a two-dimensional convolutional neural network (CNN-2d), a feature pyramid network (FPN), etc. The physical identification model may be obtained by training based on historical physical information.

The obtained physical information of the target object may be input into the trained physical identification model, and the model may output the abnormal physical information of the target object. In this way, the abnormal physical information of the target object may be obtained.

The normal physical information may be physical information of a normal state of the target object. For example, the body temperature of the target object may be 36-36.4° under a normal circumstance. If the body temperature of the target object is 37° after measurement, the physical information of the body temperature of the target object may be determined to be abnormal at this time.

Optionally, the determining the abnormal physical information by analyzing the physical information may also be: comparing the physical information with standard physical information corresponding to a type of the target object to determine the abnormal physical information that does not conform to the standard physical information.

For example, the type of the target object may be determined based on basic information of a human body and/or a historical medical record of the target object. The basic information of the human body may at least include a gender, an age, a weight, a height, and other information.

The standard physical information may be physical information corresponding to different genders, ages, weights, and heights determined by a country. For example, a male aged 45-55 years old and 170-175 cm in height may have a body temperature of 36-36.4°.

For example, the target object may be a male aged 50 and 172 cm in height, and a male aged 45-55 and 170-175 cm in height. For the body temperature, the standard physical information may be 36-36.4°. If the body temperature of the target object is measured to be 37°, the physical information of the body temperature may be abnormal physical information.

The historical medical record may be historical medical information of the target object, e.g., the target object has suffered from a disease such as hypertension for many years. This may cause the physical information of the target object to be inconsistent with the normal standard physical information, but this may not mean that the physical information of the target object is abnormal. For example, for a male aged 45-55 years old and 170-175 cm in height, the standard physical information for the body temperature may be 36-36.4°. If a patient is a 50 years old male with hypertension and a height of 172 cm, and the body temperature of the patient is measured to be 35.7°, the body temperature may be normal for the patient with hypertension, and therefore, the body temperature may not be the abnormal physical information.

Thus, the abnormal physical information in the physical information of the target object may be determined by the above three ways, so that the abnormal physical information of the target object may be determined quickly and the diagnostic efficiency may be improved.

When the physical information of the target object is obtained, the physical information of the target object may be analyzed so as to determine the abnormal physical information of the target object. In this way, the abnormal physical information of the target object may be quickly determined so that the scanning parameter and/or the image processing parameter of the medical imaging device may be adjusted pertinently based on the abnormal physical information.

In operation 1330, a scanning parameter and/or an image processing parameter of the medical imaging device may be determined adaptively based on the abnormal physical information of the target object.

For example, the scanning parameter may be a scanning parameter for image scanning of the target object, for example, may be a scanning parameter for performing a magnetic resonance scan or a scanning parameter for performing an electronic computer tomography scan, etc., on the target object. Specifically, the scanning parameter may be a scanning voltage, a scanning current, a scanning view field, a number of scanning layers, a scanning layer thickness, etc. For example, if the target object has a relatively high body temperature, a voltage parameter may be reduced and a current parameter may be increased, etc.

The image processing parameter may be a parameter for processing a scanning algorithm of a region of interest of the target object. The region of interest may be a region where the target object may have an abnormality determined by the abnormal physical information. For example, if the body temperature of the target object is relatively high, the lungs of the target object may have an abnormality, and the lungs may be determined as the region of interest of the target object.

The image processing parameter may be a parameter for processing the scanning algorithm of the region of interest of the target object. For example, a magnetic resonance scan may be performed on the target object to be scanned, and the abnormal physical information may be an abnormal body temperature. For example, if the body temperature is relatively high, an image of the lungs may be processed. For example, the image processing parameter for the image of the lungs may be adjusted. For example, a contrast level and an equalization level of soft tissue and bone tissue in the lungs, etc., may be adjusted. Specifically, the intensity of the equalization level may be reduced and the enhancement intensity of the contrast level may be increased, which may make the lung texture of the target object clearer, and a clearer and more targeted scanned image may be obtained.

Optionally, the medical imaging device may include, but is not limited to, an X-ray camera device, an MR device, a CT device, a PET device, an ultrasound device, a DSA device, or a multi-modality imaging device.

Specifically, if the abnormal physical information is the body temperature, for example, the body temperature is relatively high, for the scanning parameter, the scanning voltage may be reduced and the scanning current may be increased. For the image processing parameter, the image equalization level may be reduced and the image contrast level may be increased.

If the abnormal physical information is the respiratory information, for example, the breathing is relatively rapid, for the scanning parameter, the scanning voltage may be reduced and the scanning current may be increased. For the image processing parameter, the image equalization level may be reduced and the image contrast level may be increased.

If the abnormal physical information is the eye physical information, for example, the white eyes turns yellow, for the scanning parameter, the scanning voltage may be reduced and the scanning current may be increased. For the image processing parameter, the image equalization level may be increased and the image contrast level may be decreased.

It should be noted that the determining the scanning parameter and/or the image processing parameter of the medical imaging device adaptively may be adjusting the scanning parameter and/or the image processing parameter of the medical imaging device according to a condition of the target object. The term "adaptively" used herein may be to achieve matching the abnormal physical information with the scanning parameter and/or the image processing parameter.

It should be noted that the determining the scanning parameter and/or the image processing parameter of the medical imaging device based on the abnormal physical information of the target object may be determining the scanning parameter and/or the image processing parameter of the target object by inputting the abnormal physical information of the target object into a neural network model or a corresponding database. In this way, the scanning parameter and/or the image processing parameter of the target object may be obtained quickly, thus improving the efficiency of diagnosis.

In this way, the scanning parameter and/or the image processing parameter of the target object may be determined based on the abnormal physical information of the target object. It solves the problem that a doctor needs to constantly adjust the scanning parameter and/or the image processing parameter in prior arts, resulting in poor image quality, repeated scanning, low efficiency, and affecting the diagnosis, and at the same time, it may avoid the problem that the target object receives too much radiation dose. In this way, the scanning parameter of medical imaging device may be determined in time based on the target physical information to achieve the purpose of improving the diagnostic efficiency.

In the technical solution of the embodiments of the present disclosure, the physical information of the target object may be obtained. The abnormal physical information may be determined by analyzing the physical information. The scanning parameter and/or the image processing parameter of the medical scanning imaging device may be determined based on the abnormal physical information of the target object. In this way, the scanning parameter of medical imaging device may be determined in time based on the target physical information to achieve the purpose of improving the diagnostic efficiency. It solves the problem that a doctor needs to constantly adjust the scanning parameter and/or the image processing parameter in prior arts, resulting in poor image quality, repeated scanning, low efficiency, and affecting the diagnosis, and at the same time, it may avoid the problem that the target object receives too much radiation dose.

Figure 14:
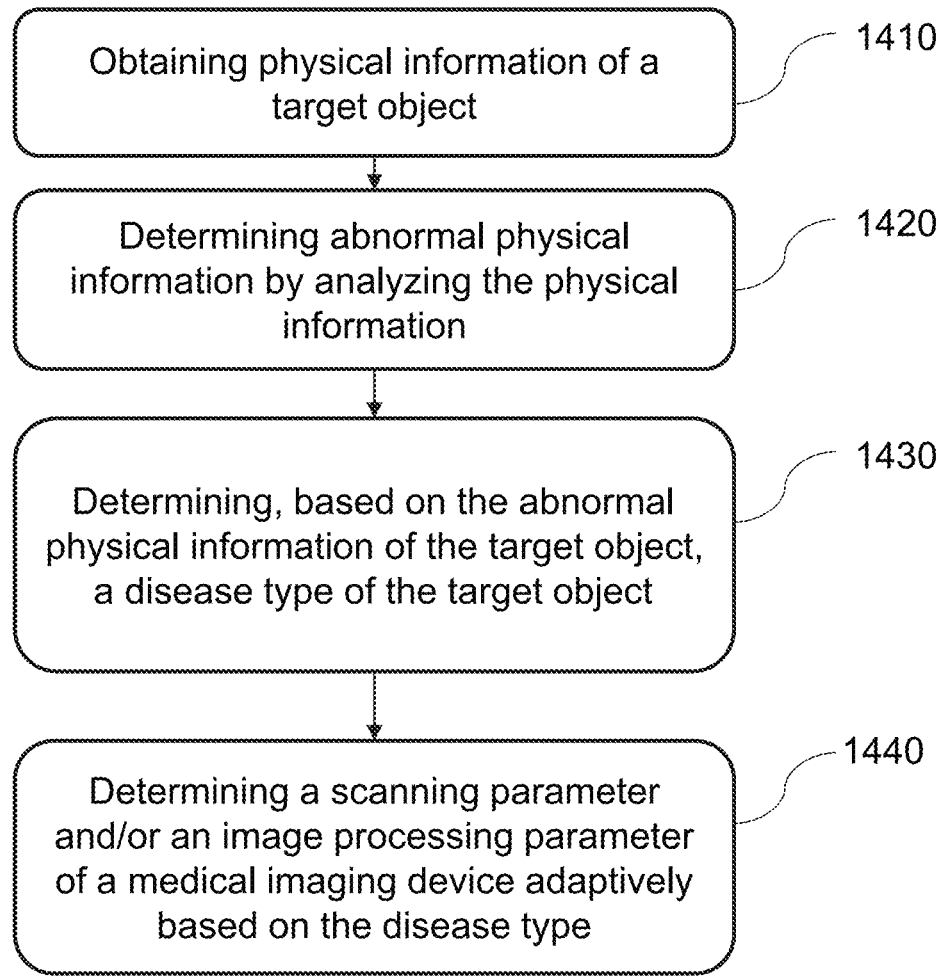
FIG. 14 is a flowchart illustrating an exemplary process for determining a parameter of a medical imaging device according to some embodiments of the present disclosure.

FIG. 14 is a flowchart illustrating an exemplary process for determining a parameter of a medical imaging device according to some embodiments of the present disclosure. The embodiments of the present disclosure may be combined with various optional embodiments in the above embodiments. Optionally, in the embodiments of the present disclosure, the determining the scanning parameter and/or the image processing parameter of the medical imaging device adaptively based on the abnormal physical information of the target object may include: determining, based on the abnormal physical of the target object, a disease type of the target object; and determining the scanning parameter and/or the image processing parameter of the medical imaging device adaptively based on the disease type.

As shown in FIG. 14, the process 1400 in some embodiments of the present disclosure may specifically include the following operations.

In operation 1410, physical information of a target object may be obtained.

In operation 1420, abnormal physical information may be determined by analyzing the physical information.

In operation 1430, a disease type of the target object may be determined based on the abnormal physical information of the target object.

For example, the disease type may be a disease that may exist in the target object determined based on the abnormal physical information. For example, if the body temperature of the target object is relatively high, the target object may have an abnormality in the lungs, and it may be determined that target object has pneumonia and other lung diseases. As another example, if the breathing of the target object is relatively rapid, the target object may have an abnormality in the respiratory tract, and it may be determined that the target object has asthma and other diseases. As another example, if the white eyes of the target object turns yellow, the target object may have an abnormality in the eyes, and it may be determined that the target object has a liver lesion and other diseases.

In this way, the disease type of the target object may be directly determined based on the abnormal physical information, and the scanning parameter and/or the image processing parameter may be adjusted based on the disease type.

In operation 1440, a scanning parameter and/or an image processing parameter of the medical imaging device may be determined adaptively based on the disease type.

For example, the scanning parameter and/or the image processing parameter of the target object may be adjusted pertinently and adaptively based on the determined disease type, to obtain an accurate and targeted scanned image. In this way, the scanning parameter may be determined in time based on the physical information of the target object to achieve the purpose of improving the diagnostic efficiency. It solves the problem that a doctor needs to constantly adjust the scanning parameter and/or the image processing parameter in prior arts, resulting in poor image quality, repeated scanning, low efficiency, and affecting the diagnosis.

Optionally, the determining the scanning parameter and/or the image processing parameter of the medical imaging device adaptively based on the disease type may specifically include: determining an abnormality level of the abnormal physical information; and determining the scanning parameter and/or the image processing parameter of the medical imaging device adaptively based on the disease type and the abnormality level.

For example, the abnormality level may be a level of the abnormal physical information. For example, the body temperature of the target object may be 38°, a standard body temperature may be 36-37°, 37-37.5° may be determine as a mild fever, 37.6-38° may be determine as a moderate fever, and 38° or higher may be determine as a severe fever. Accordingly, the abnormality level of the target object may be determined as the moderate fever.

It may be determined that the target object has pneumonia based on the body temperature of the target object. The scanning parameter and/or the image processing parameter of the target object may be adjusted based on the determined pneumonia and the determined moderate fever of the target object.

It should be noted that the scanning parameters and/or the image processing parameters for different disease types may be different. The scanning parameters and/or the image processing parameters for different abnormality levels for a same disease type may also be different. Therefore, the scanning parameter and/or the image processing parameter of the medical imaging device may be determined pertinently based on the disease type and the abnormality level, to obtain an accurate and targeted scanned image, so that the physician can diagnose based on the image better.

In the technical solution of the embodiments of the present disclosure, the disease type of the medical imaging device may be determined based on the abnormal physical information of the target object. The scanning parameter and/or the image processing parameter of the medical imaging device may be determined adaptively based on the disease type, to obtain an accurate and targeted scanned image. In this way, the scanning parameter of medical imaging device may be determined in time based on the physical information of the target object to achieve the purpose of improving the diagnostic efficiency. It solves the problem that a doctor needs to constantly adjust the scanning parameter and/or the image processing parameter in prior arts, resulting in poor image quality, repeated scanning, low efficiency, and affecting the diagnosis.

Figure 15:
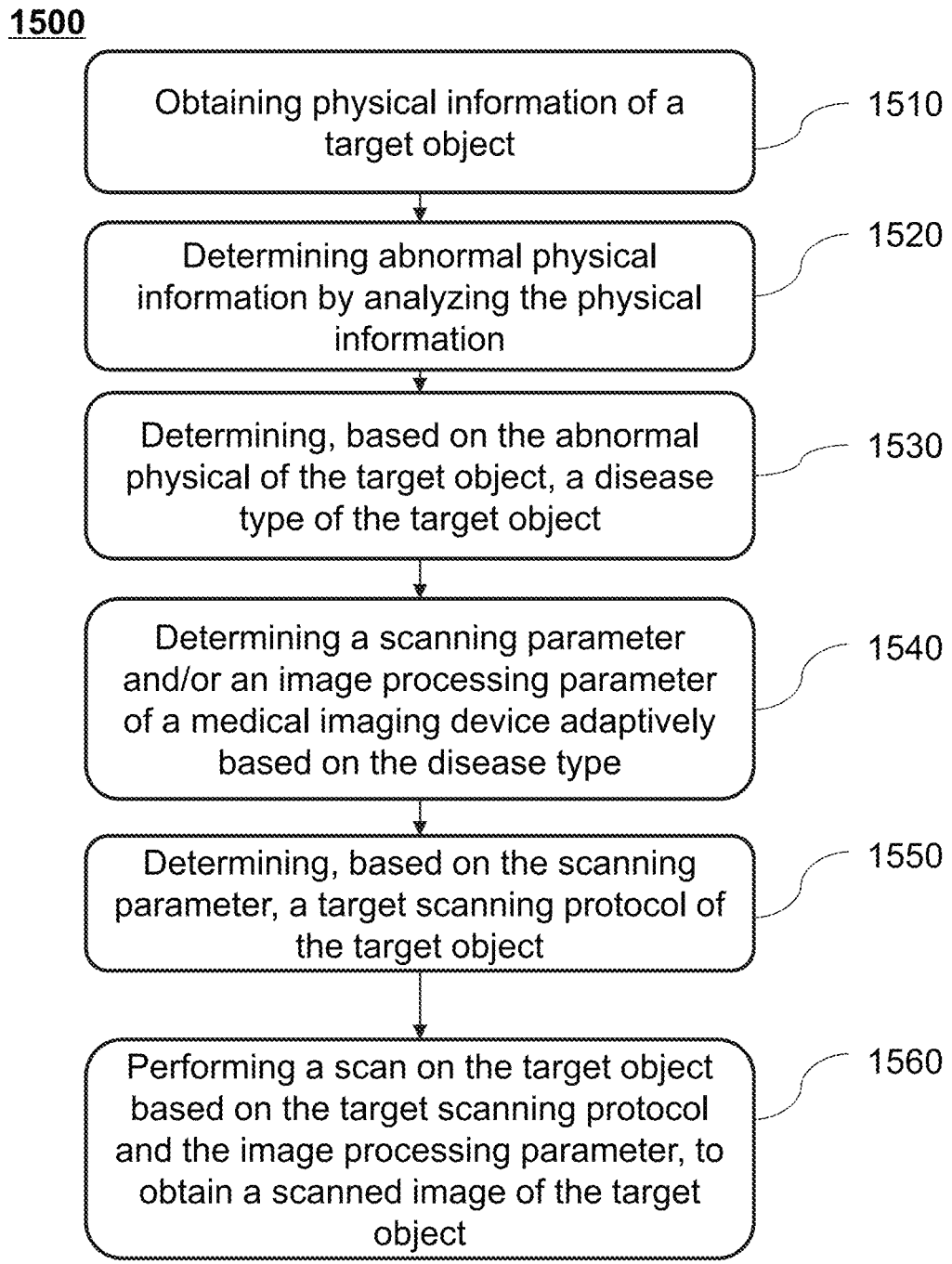
FIG. 15 is a flowchart illustrating an exemplary process for determining a parameter of a medical imaging device according to some embodiments of the present disclosure.

FIG. 15 is a flowchart illustrating an exemplary process for determining a parameter of a medical imaging device according to some embodiments of the present disclosure. The embodiments of the present disclosure may be combined with various optional embodiments in the above embodiments. Optionally, in the embodiments of the present disclosure, the method may further include: determining, based on the scanning parameter, a target scanning protocol of the target object; and performing a scan on the target object based on the target scanning protocol and the image processing parameter, to obtain a scanned image of the target object.

As shown in FIG. 15, the process 1500 in some embodiments of the present disclosure may specifically include the following operations.

In operation 1510, physical information of a target object may be obtained.

In operation 1520, abnormal physical information may be determined by analyzing the physical information.

In operation 1530, a disease type of the target object may be determined based on the abnormal physical of the target object.

In operation 1540, a scanning parameter and/or an image processing parameter of the medical imaging device may be determined adaptively based on the disease type.

In operation 1550, a target scanning protocol of the target object may be determined based on the scanning parameter.

For example, the target scanning protocol may be a scanning protocol that is ultimately used to perform an image scan on the target object. After the scanning parameter of the target object is determined, the target scanning protocol of the target object may be generated.

In operation 1560, a scan may be performed on the target object based on the target scanning protocol and the image processing parameter, to obtain a scanned image of the target object.

For example, the image scan may be performed on the target object based on the target scanning protocol and the image processing parameter, and a targeted, high-quality and effective scan image that can well reflect the anomaly of the target object may be obtained.

It should be noted that when the target object is scanned based on the target scanning protocol and the image processing parameter, a whole body scan may be performed on the target object, and an abnormal part of the target object may be highlighted. For example, if it is determined that the target object may have pneumonia, when the target object is scanned based on the target scanning protocol and the image processing parameter, the whole body scan may be performed on the target object, and the clear lung texture may be highlighted in the image. The abnormal part of the target object may only be scanned. For example, if it is determined that the target object may have pneumonia, when the target object is scanned based on the target scanning protocol and the image processing parameter, only the lungs of the target object may be scanned, and the clear lung textures may be highlighted. Whether to scan the whole body of the target object or only scan the abnormal part of the target object may be determined according to the user's needs, which is not limited here.

In the technical solution of the embodiments of the present disclosure, the target scanning protocol of the target object may be determined based on the scanning parameter, and the scan may be performed on the target object based on the target scanning protocol and the image processing parameter, to obtain the scanned image of the target object. In this way, a targeted, high-quality and effective scan image that can well reflect the anomaly of the target object may be obtained.

Figure 16:
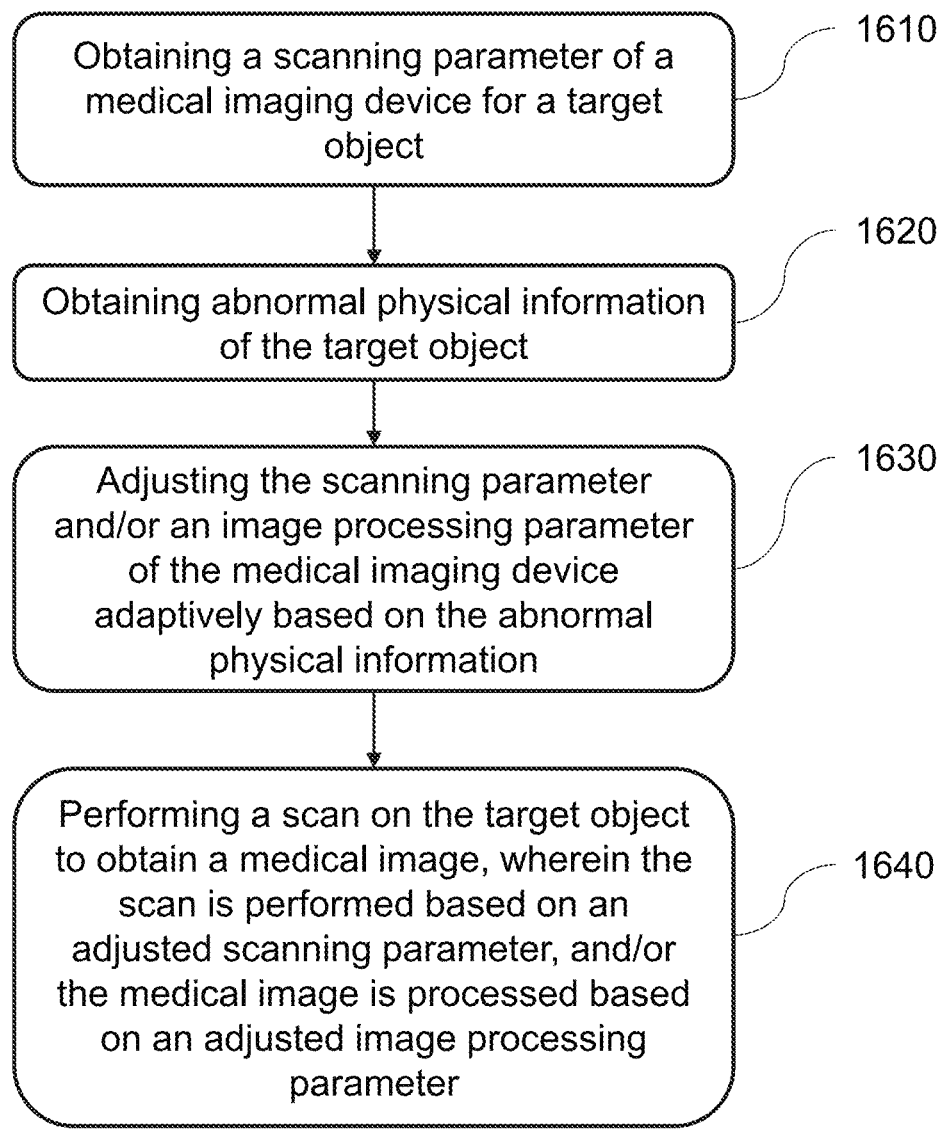
FIG. 16 is a flowchart illustrating an exemplary imaging process of a medical imaging device according to some embodiments of the present disclosure.

FIG. 16 is a flowchart illustrating an exemplary imaging process of a medical imaging device according to some embodiments of the present disclosure. The embodiments may be applicable to a case where the scanning parameter and the image processing parameter of the medical imaging device are determined based on the physical information of the target object, and the target object is scanned and imaged. The method may be performed by an imaging device of the medical imaging device. The imaging device of the medical imaging device may be implemented by software and/or hardware. The imaging device of the medical imaging device may be configured on a computing device. The explanations of the same or corresponding terms in the embodiments of the present disclosure and the above embodiments are not repeated herein.

Referring to FIG. 16, the imaging method 1600 of the medical imaging device in some embodiments of the present disclosure may specifically include the following operations.

In operation 1610, a scanning parameter of the medical imaging device for a target object may be obtained.

In operation 1620, abnormal physical information of the target object may be obtained.

In operation 1630, a scanning parameter and/or an image processing parameter of the medical imaging device may be adjusted adaptively based on the abnormal physical information.

In operation 1640, a scan may be performed on the target object to obtain a medical image. The scan may be performed based on an adjusted scanning parameter, and/or the medical image may be processed based on an adjusted image processing parameter.

In the technical solution of the embodiments of the present disclosure, the scanning parameter of the medical imaging device for the target object may be obtained by obtaining the abnormal physical information of the target object. The scanning parameter and/or the image processing parameter of the medical imaging device may be adjusted adaptively based on the abnormal physical information. The scan may be performed on the target object to obtain a medical image. The scan may be performed based on the adjusted scanning parameter and/or the medical image may be processed based on the adjusted image processing parameter, such that the scanning parameter of the medical imaging device can be adjusted in time based on the physical information of the target object, the scan can be performed on the target object using the adjusted scanning parameter, and then the scanned image can be processed using the adjusted image processing parameter, to obtain a better quality and clearer scanned image to achieve the purpose of improving diagnosis efficiency. It may solve the problem that a doctor needs to constantly adjust the scanning parameter and/or the image processing parameter in prior arts, resulting in poor image quality, repeated scanning, low efficiency, and affecting the diagnosis, and at the same time, it may avoid the problem that the target object receives too much radiation dose.

Figure 17:
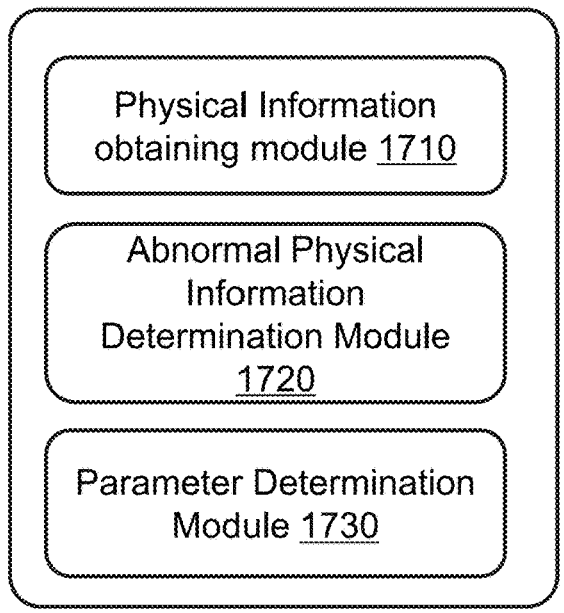
FIG. 17 is a schematic diagram illustrating an exemplary structure of a device for determining a parameter of a medical imaging device according to some embodiments of the present disclosure.

FIG. 17 is a schematic diagram illustrating an exemplary structure of a device for determining a parameter of a medical imaging device according to some embodiments of the present disclosure. As shown in FIG. 17, the device 1700 may include a physical information obtaining module 1710, an abnormal physical information determination module 1720, and a parameter determination module 1730.

The physical information obtaining module 1710 may be configured to obtain physical information of a target object.

The abnormal physical information determination module 1720 may be configured to determine abnormal physical information by analyzing the physical information.

The parameter determination module 1720 may be configured to determine a scanning parameter and/or an image processing parameter of the medical imaging device adaptively based on the abnormal physical information of the target object.

Optionally, the scanning parameter may include a scanning voltage, a scanning current, a scanning view field, a number of scanning layers, or a scanning layer thickness.

Optionally, the image processing parameter may include an image contrast level or an image equalization level.

Optionally, the obtaining the physical information of the target object may be achieved by a sensor.

Optionally, the sensor may include a camera, a temperature sensor, a heartbeat sensor, or a respiration sensor.

Based on the technical solutions of the above embodiments, the parameter determination module 1730 may include:
  a disease type determination unit configured to determine, based on the abnormal physical of the target object, a disease type of the target object;
  a parameter determination unit configured to determine the scanning parameter and/or the image processing parameter of the medical imaging device adaptively based on the disease type.

Based on the technical solutions of the above embodiments, the parameter determination unit may include:
  an abnormality level determination sub-unit configured to determine an abnormality level of the abnormal physical information;
  a parameter determination sub-unit configured to determine the scanning parameter and/or the image processing parameter of the medical imaging device adaptively based on the disease type and the abnormality level.

Based on the technical solutions of the above embodiments, the abnormal physical information determination module 1720 may include:
  a first abnormal physical information determination unit configured to input the physical information into a trained physical identification model, and obtain the abnormal physical information output by the physical identification model;
  or,
  a third abnormal physical information determination unit configured to compare the physical information with a normal physical parameter to determine the abnormal physical information.

Based on the technical solutions of the above embodiments, the abnormal physical information determination module 1720 may further include:
  a second abnormal physical information determination unit configured to compare the physical information with standard physical information corresponding to a type of the target object to determine the abnormal physical information that does not conform to the standard physical information; wherein the type of the target object may be determined based on basic information of a human body and/or a historical medical record of the target object, and the basic information of the human body may include at least one of a gender, an age, a weight, or a height.

Based on the technical solutions of the above embodiments, the device may further include:
  a target scanning protocol determination module configured to determine, based on the scanning parameter, a target scanning protocol of the target object;
  a scanned image obtaining module configured to perform a scan on the target object based on the target scanning protocol and the image processing parameter, to obtain a scanned image of the target object.

Optionally, the image processing parameter may be a parameter for processing a scanning algorithm for a region of interest of the target object.

The device for determining the parameter of the medical imaging device provided in some embodiments of the present disclosure may implement the method for determining the parameter of the medical imaging device provided in any embodiment of the present disclosure, and may have corresponding functional modules and beneficial effects of the implementation method.

Figure 18:
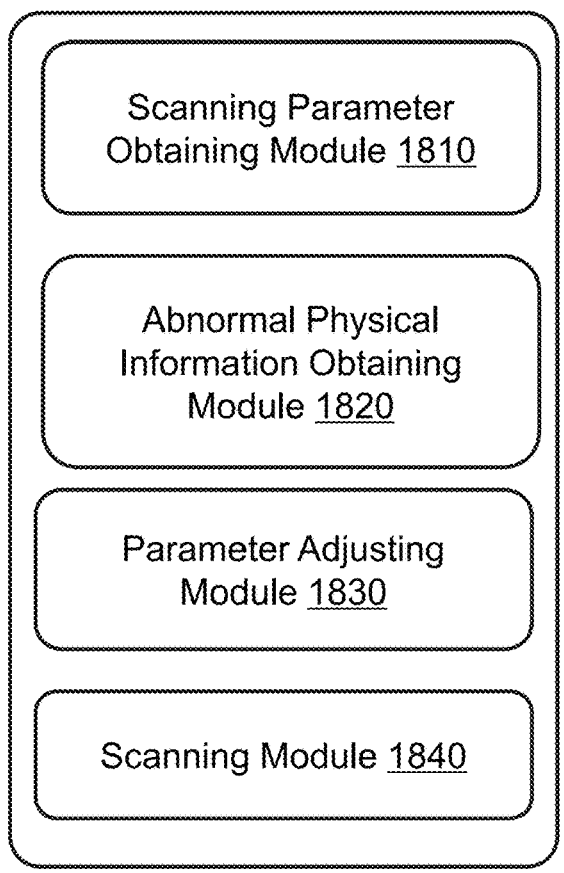
FIG. 18 is a schematic diagram illustrating an exemplary structure of an imaging device for a medical imaging device according to some embodiments of the present disclosure.

FIG. 18 is a schematic diagram illustrating an exemplary structure of an imaging device for a medical imaging device according to some embodiments of the present disclosure. As shown in FIG. 18, the device 1800 may include: a scanning parameter obtaining module 1810, an abnormal physical information obtaining module 1820, a parameter adjusting module 1830, and a scanning module 1840.

The scanning parameter obtaining module 1810 may be configured to obtain a scanning parameter of the medical imaging device for a target object.

The abnormal physical information obtaining module 1820 may be configured to obtain abnormal physical information of the target object.

The parameter adjusting module 1830 may be configured to adjust the scanning parameter and/or the image processing parameter of the medical imaging device adaptively based on the abnormal physical information.

The scanning module 1840 may be configured to perform a scan on the target object to obtain a medical image. The scan may be performed based on an adjusted scanning parameter, and/or the medical image may be processed based on an adjusted image processing parameter.

The imaging device of the medical imaging device provided by some embodiments of the present disclosure may implement the imaging method of the medical imaging device provided by any embodiment of the present disclosure, and may have corresponding functional modules and beneficial effects of the implementation method.

Figure 19:
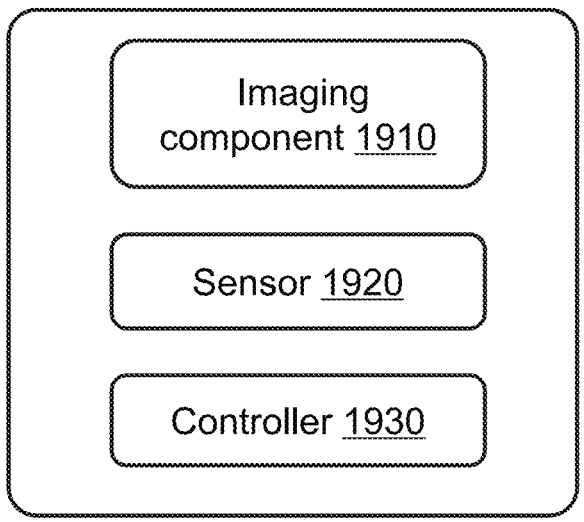
FIG. 19 is a schematic diagram illustrating an exemplary structure of a medical imaging device according to some embodiments of the present disclosure.

FIG. 19 is a schematic diagram illustrating an exemplary structure of a medical imaging device according to some embodiments of the present disclosure. As shown in FIG. 19, the medical imaging device 1900 may include an imaging component 1910, a sensor 1920, and a controller 1930.

The imaging component 1910 may be configured to scan a target object to obtain a medical image.

The sensor 1920 may be configured to obtain abnormal physical information of the target object.

The controller 1930 may be coupled to the imaging assembly and the sensor, and may be configured to adjust a scanning parameter of the imaging component adaptively based on the abnormal physical information, and/or adjust an image processing parameter of the medical image adaptively based on the abnormal physical information.

Optionally, the sensor may include a camera, a temperature sensor, a heartbeat or pulse sensor, or a respiration sensor.

Figure 20:
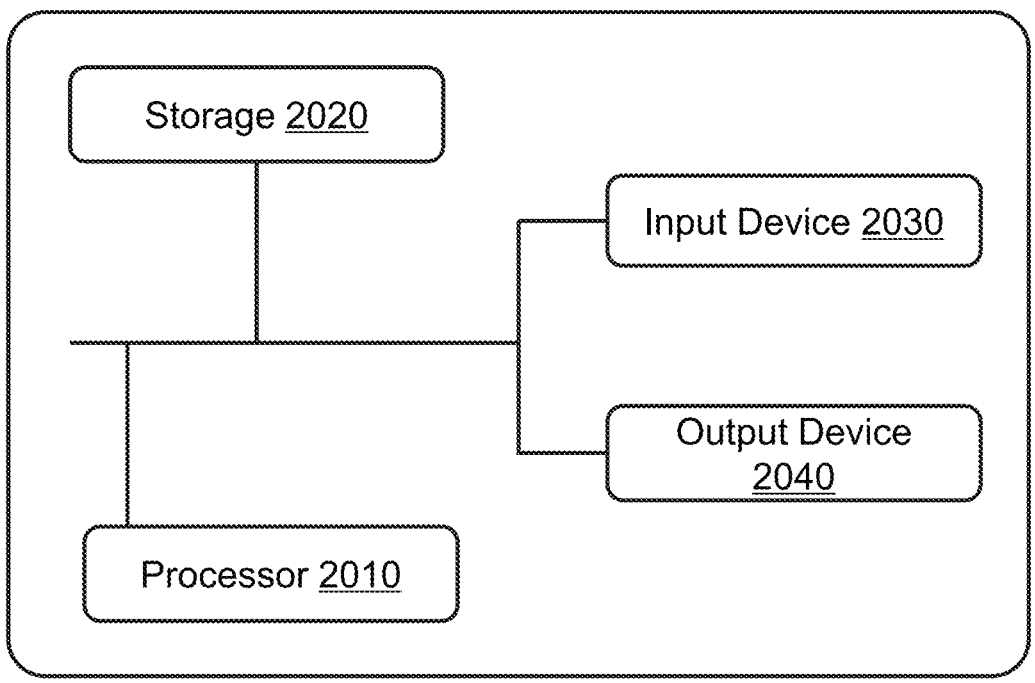
FIG. 20 is a schematic diagram illustrating an exemplary structure of a device according to some embodiments of the present disclosure.

FIG. 20 is a schematic diagram illustrating an exemplary structure of a device according to some embodiments of the present disclosure. As shown in FIG. 20, the device 2000 may include a processor 2010, a storage 2020, an input device 2030, and an output device 2040. A number of the processors 2010 in the device may be one or more. Take one processor 2010 as an example in FIG. 20. The processors 2010, the storage 2020, the input device 2030, and the output device 2040 of the device may be connected via a bus or other manners. Take a bus connection as an example in FIG. 20.

The storage 2020, as a computer-readable storage medium, may be used to store software programs, computer-executable programs, and modules, such as program instructions/modules corresponding to the method for determining a parameter of the medical imaging device in some embodiments of the present disclosure (e.g., the physical information obtaining module 1710, the abnormal physical information determination module 1720, and the parameter determination module 1730), and/or the program instructions/modules corresponding to the imaging method of the medical imaging device (e.g., the scanning parameter obtaining module 1810, the abnormal physical information obtaining module 1820, the parameter adjusting module 1830, and the scanning module 1840). The processor 2010 may perform various functional applications of the device and data processing by running the software programs, instructions, and modules stored in the storage 2020, i.e., to implement the method for determining a parameter described above.

The storage 2020 may mainly include a storage program region and a storage data region. The storage program region may store an operating system, an application program required for at least one function. The storage data region may store data created based on the use of the terminal, etc. In addition, the storage 2020 may include a high-speed random access storage, and may also include a non-volatile storage, such as at least one disk storage device, a flash storage device, or other non-volatile solid state storage device. In some embodiments, the storage 2020 may further include a storage that are remotely located relative to the processor 2010. The remote storage may be connected to the device via a network. Examples of the networks may include, but is not limited to, the Internet, an enterprise intranet, a local area network, a mobile communication network, or any combinations thereof.

The input device 2030 may be used to receive input numeric or character information, and to generate a key signal input related to a user setting of the device and a functional control. The output device 2040 may include a display device such as a display screen.

The ninth embodiment of the present disclosure may further provide a storage medium including computer executable instructions. When executed by a computer processor, the computer-executable instructions may be used to execute a method for determining a parameter of a medical imaging device, and/or an imaging method of a medical imaging device.

Of course, the embodiments of the present disclosure may provide a storage medium including computer executable instructions. The computer executable instructions may not be limited to the operations of the method as described above, but may also perform the relevant operations in the method for determining a parameter of a medical imaging device and/or the imaging method of a medical imaging device provided in any embodiment of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C, C, or the like. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network (including a local area network (LAN) or a wide area network (WAN)), or the connection may be made to an external computer (for example, through the Internet using an Internet Service Provider) or in a cloud computing environment or offered as a service (such as a Software as a Service (SaaS)).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for controlling a medical device, comprising:
    obtaining position information of one or more ionization chambers of a scanning device, the scanning device being configured to scan a target object;
    determining a detection region of at least one ionization chamber of the one or more ionization chambers based on the position information of the one or more ionization chambers;
    determining projection data of a projection device, the projection data including image data corresponding to the detection region of the at least one ionization chamber;
    controlling the projection device to project the projection data onto the target object;
    obtaining a reference image of the target object, the reference image being captured by a camera after the projection device projects the projection data onto the target object to be scanned, and the reference image including a projection region corresponding to the detection region of the at least one ionization chamber and a region of interest to be scanned of the target object; and
    determining, from the one or more ionization chambers based on the projection region and the region of interest in the reference image, one or more target ionization chambers to be operated during a scan of the target object.

2. The method of claim 1, wherein the determining, from the one or more ionization chambers based on the reference image, one or more target ionization chambers comprises:
    identifying a first region in the reference image, the first region corresponding to the region of interest;
    identifying a second region in the reference image, the second region corresponding to the detection region of the at least one ionization chamber projected onto the target object; and
    determining, based on the first region and the second region, whether the at least one ionization chamber includes one or more candidate ionization chambers, wherein detection regions of the one or more candidate ionization chambers are covered by the region of interest to be scanned of the target object.

3. The method of claim 2, wherein the determining, from the one or more ionization chambers based on the reference image, one or more target ionization chambers comprises:
    in response to determining that the at least one ionization chamber does not include any candidate ionization chamber, causing a terminal device to generate prompt information; or
    in response to determining that the at least one ionization chamber does not include any candidate ionization chamber, causing one or more reference ionization chambers of the at least one ionization chamber to be moved relative to the region of interest of the target object.

4. The method of claim 1, wherein the method further comprises:
    obtaining identification information of the one or more target ionization chambers selected from the at least one ionization chamber; and
    adjusting the projection data based on the identification information, such that a first feature value of image data corresponding to detection regions of the one or more target ionization chambers in the projection data is different from a second feature value of image data corresponding to detection regions of other ionization chambers, wherein the first feature value and the second feature value correspond to a same image feature.

5. The method of claim 1, wherein the method further comprises:
    obtaining a model of an X-ray camera gantry based on a solid structure of the X-ray camera gantry;
    simulating a corresponding model movement trajectory by using the model of the X-ray camera gantry based on a movement trajectory of the solid structure of the X-ray camera gantry; and
    obtaining a movement instruction of the solid structure of a current X-ray camera gantry, the movement instruction including a target position that a component of the current X-ray camera gantry needs to move to and related movement time information;
    causing the the solid structure of the X-ray camera gantry to reach the target position based on the movement instruction;
    simulating, by the model of the X-ray camera gantry, a movement trajectory of the model based on the movement instruction and the movement time information synchronously; and
    displaying a simulation of the movement trajectory of the model on a display device.

6. The method of claim 5, wherein the model is obtained according to a process including:
    obtaining an image of the X-ray camera gantry;
    extracting a feature point of the image; and obtaining the model by reconstructing the model based on the feature point.

7. The method of claim 1, further comprising:
obtaining physical information of the target object;
determining abnormal physical information by analyzing the physical information; and
determining a scanning parameter and/or an image processing parameter of the scanning device adaptively based on the abnormal physical information of the target object.

8. The method of claim 7, wherein the determining a scanning parameter and/or an image processing parameter of the scanning device adaptively based on the abnormal physical information of the target object comprises:
determining, based on the abnormal physical information of the target object, a disease type of the target object; and
determining the scanning parameter and/or the image processing parameter of the scanning device adaptively based on the disease type.

9. The method of claim 1, wherein the projection data further includes image data corresponding to the region of interest to be scanned of the object.

10. The method of claim 9, wherein different projection modes are used to project the image data corresponding to the detection region and the image data corresponding to the region of interest for distinguishing the region of interest and the detection region.

11. The method of claim 2, wherein the determining, from the one or more ionization chambers based on the reference image, one or more target ionization chambers further comprises:
in response to determining that the at least one ionization chamber includes one or more candidate ionization chambers, selecting the one or more target ionization chambers close to the region of interest from the one or more candidate ionization chambers based on a distance between each of the one or more candidate ionization chamber and the region of interest.

12. The method of claim 1, wherein an ionization chamber whose detection regions in the reference image is covered by the region of interest in the reference image and close to the region of interest in the reference image is selected from the at least one ionization chamber as the one or more target ionization chambers.

13. A method for marking a detection region of an ionization chamber, wherein the method comprises:
obtaining position information of one or more ionization chambers of a scanning device, the scanning device being configured to scan an object;
determining a detection region of at least one ionization chamber of the one or more ionization chambers based on the position information of the one or more ionization chambers;
determining projection data of a projection device, the projection data including image data corresponding to the detection region of the at least one ionization chamber and image data corresponding to a region of interest to be scanned of the target object;
controlling the projection device to project the projection data onto the object;
obtaining a reference image of the target object, the reference image being captured by a camera after the projection device projects the projection data onto the target object to be scanned and including projected data of the projection device;
determining, from the one or more ionization chambers based on the reference image, one or more target ionization chambers to be operated during a scan of the target object.

14. The method of claim 13, wherein the determining, from the one or more ionization chambers based on the reference image, one or more target ionization chambers comprises:
identifying a first region in the reference image, the first region corresponding to the region of interest to be scanned of the object;
identifying a second region in the reference image, the second region corresponding to the detection region of at least one ionization chamber projected onto the object; and
determining, based on the first region and the second region, whether the at least one ionization chamber includes one or more candidate ionization chambers, wherein detection regions of the one or more candidate ionization chambers are covered by the region of interest to be scanned of the object.

15. The method of claim 14, wherein the determining, from the one or more ionization chambers based on the reference image, one or more target ionization chambers further comprises:
in response to determining that the at least one ionization chamber does not include any candidate ionization chamber, causing a terminal device to generate prompt information.

16. The method of claim 14, wherein the determining, from the one or more ionization chambers based on the reference image, one or more target ionization chambers further comprises:
in response to determining that the at least one ionization chamber does not include any candidate ionization chamber,
causing one or more reference ionization chambers of the at least one ionization chamber to be moved relative to the region of interest of the object.

17. The method of claim 14, wherein the determining, from the one or more ionization chambers based on the reference image, one or more target ionization chambers further comprises:
in response to determining that the at least one ionization chamber includes one or more candidate ionization chambers, selecting the one or more target ionization chambers from the one or more candidate ionization chambers, wherein the one or more target ionization chambers operate during a scan of the object.

18. The method of claim 13, wherein the method further comprises:
obtaining identification information of one or more target ionization chambers selected from the at least one ionization chamber; and
adjusting the projection data based on the identification information, such that a first feature value of image data corresponding to detection regions of the one or more target ionization chambers in the projection data is different from a second feature value of image data corresponding to detection regions of other ionization chambers, wherein the first feature value and the second feature value correspond to a same image feature.

19. A method for controlling a medical treatment device, wherein the method comprises:
obtaining a virtual model of the medical treatment device, wherein the medical treatment device includes at least one movable first component, and accordingly the virtual model includes a second component simulating the first component, a device coordinate system in which the first component is located has a mapping relationship with a model coordinate system in which the second component is located;

obtaining current movement information of the first component of the medical treatment device; and controlling the second component of the virtual model to perform a same movement as the first component of the medical treatment device based on the current movement information of the first component of the medical treatment device.

20. The method of claim 19, the method further comprising:

pausing a movement of the second component of the virtual model on the display device, and suspending a movement of the at least one movable first component of the medical treatment device correspondingly.

* * * * *